(12) United States Patent
Takeshima

(10) Patent No.: US 12,268,542 B2
(45) Date of Patent: Apr. 8, 2025

(54) INFORMATION PROCESSING APPARATUS AND METHOD

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 692 days.

(21) Appl. No.: 17/456,960

(22) Filed: Nov. 30, 2021

(65) Prior Publication Data

US 2022/0175334 A1 Jun. 9, 2022

(30) Foreign Application Priority Data

Dec. 4, 2020 (JP) .................................. 2020-201879
Nov. 25, 2021 (JP) .................................. 2021-191450

(51) Int. Cl.
  *G06T 11/00* (2006.01)
  *A61B 6/00* (2006.01)

(52) U.S. Cl.
  CPC .......... *A61B 6/5205* (2013.01); *A61B 6/5258* (2013.01); *G06T 11/006* (2013.01); *G06T 2211/421* (2013.01); *G06T 2211/424* (2013.01)

(58) Field of Classification Search
  CPC .... A61B 6/5205; A61B 6/5258; G06T 11/006
  See application file for complete search history.

(56) References Cited

PUBLICATIONS

S.G. Lingala et al. "Accelerated dynamic MRI exploiting sparsity and low-rank structure: k-t SLR", IEEE Trans Med Imaging, May 2011 (26 pages).
H. K. Aggarwal et al. "MoDL: Model Based Deep Learning Architecture for Inverse Problems", arXiv: 1712.02862v4 [cs.CV] Jun. 5, 2019 (12 pages).
H. Pedersen et al. "k-t PCA: Temporally Constrained k-t BLAST Reconstruction Using Principal Component Analysis", Magnetic Resonance in Medicine, 2009 (11 pages).

*Primary Examiner* — Sam Bhattacharya
(74) *Attorney, Agent, or Firm* — Oblon, McClelland, Maier & Neustadt, L.L.P.

(57) ABSTRACT

According to one embodiment, an information processing apparatus includes processing circuitry. The processing circuitry calculates a plurality of bases by performing a basis conversion on signal data. The processing circuitry selects one or more specific bases with contribution rates lower than a reference from among the bases. The processing circuitry executes data processing utilizing the specific bases.

24 Claims, 16 Drawing Sheets

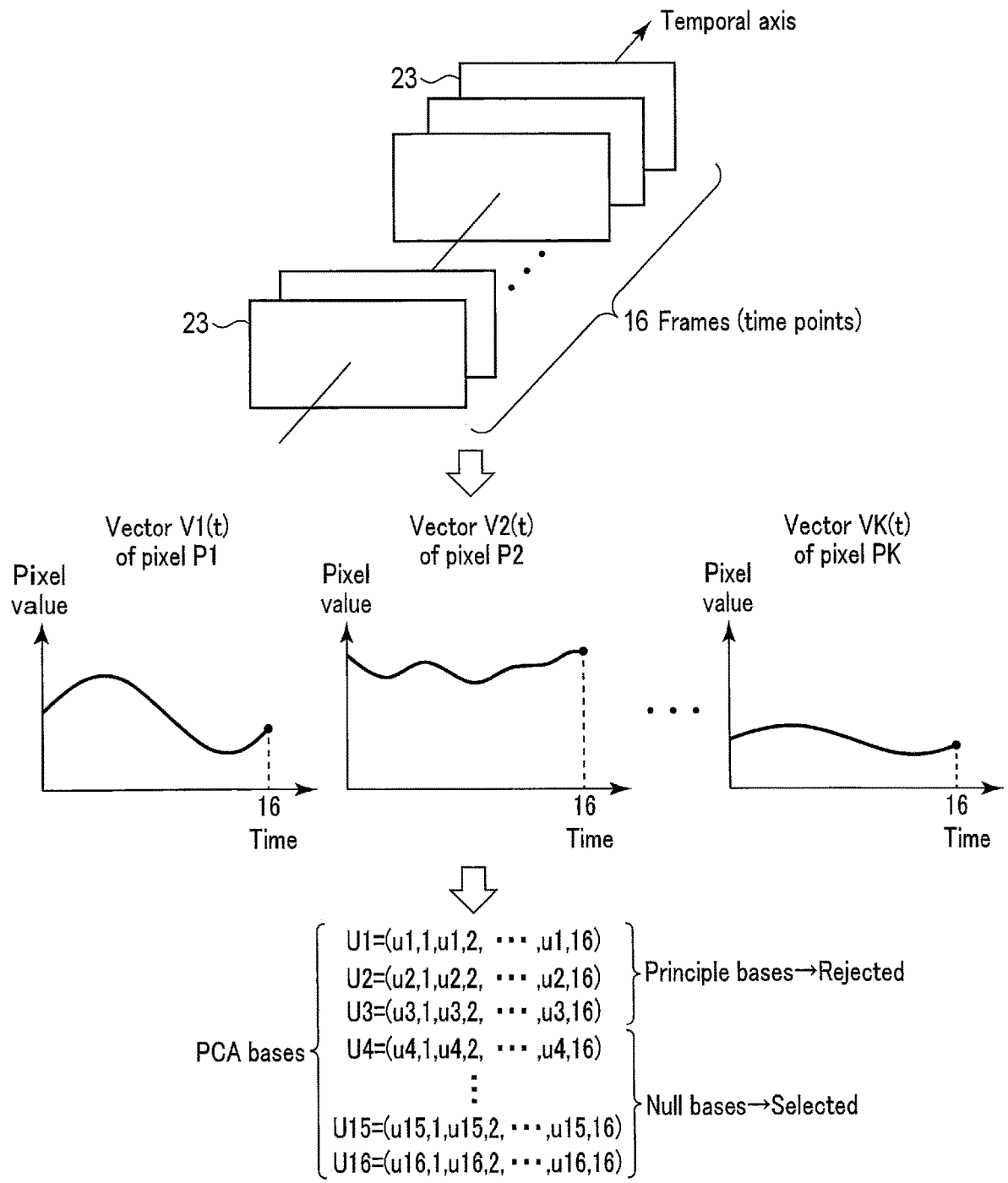
F I G. 5

  
(A) Sparse sampling
Null-space-constraint
reconstruction
Three principle bases rejected
Acceleration rate = 2.5
(B) Sparse sampling
Zero filling
Acceleration rate = 2.5
(C) Full sampling
F I G. 6

INFORMATION PROCESSING APPARATUS AND METHOD

CROSS-REFERENCE TO RELATED APPLICATIONS

This application is based upon and claims the benefit of priority from Japanese Patent Application No. 2020-201879, filed Dec. 4, 2020, and No. 2021-191450, filed Nov. 25, 2021; the entire contents of all of which are incorporated herein by reference.

FIELD

Embodiments described herein relate generally to an information processing apparatus and method.

BACKGROUND

A technology of applying a Karhunen-Loeve (KL) expansion to time-series MRI data to obtain a principle basis (basis with a relatively high contribution rate) and extracting a correlation among time-series MRI data by using the principle basis is known.

BRIEF DESCRIPTION OF THE DRAWINGS

FIG. 5 schematically shows processes of steps SA2 to SA4 in FIG. 3.

FIG. 6 shows output images of First Example (A), Comparative Example (B), and Comparative Example (C).

DETAILED DESCRIPTION

Figure 1:
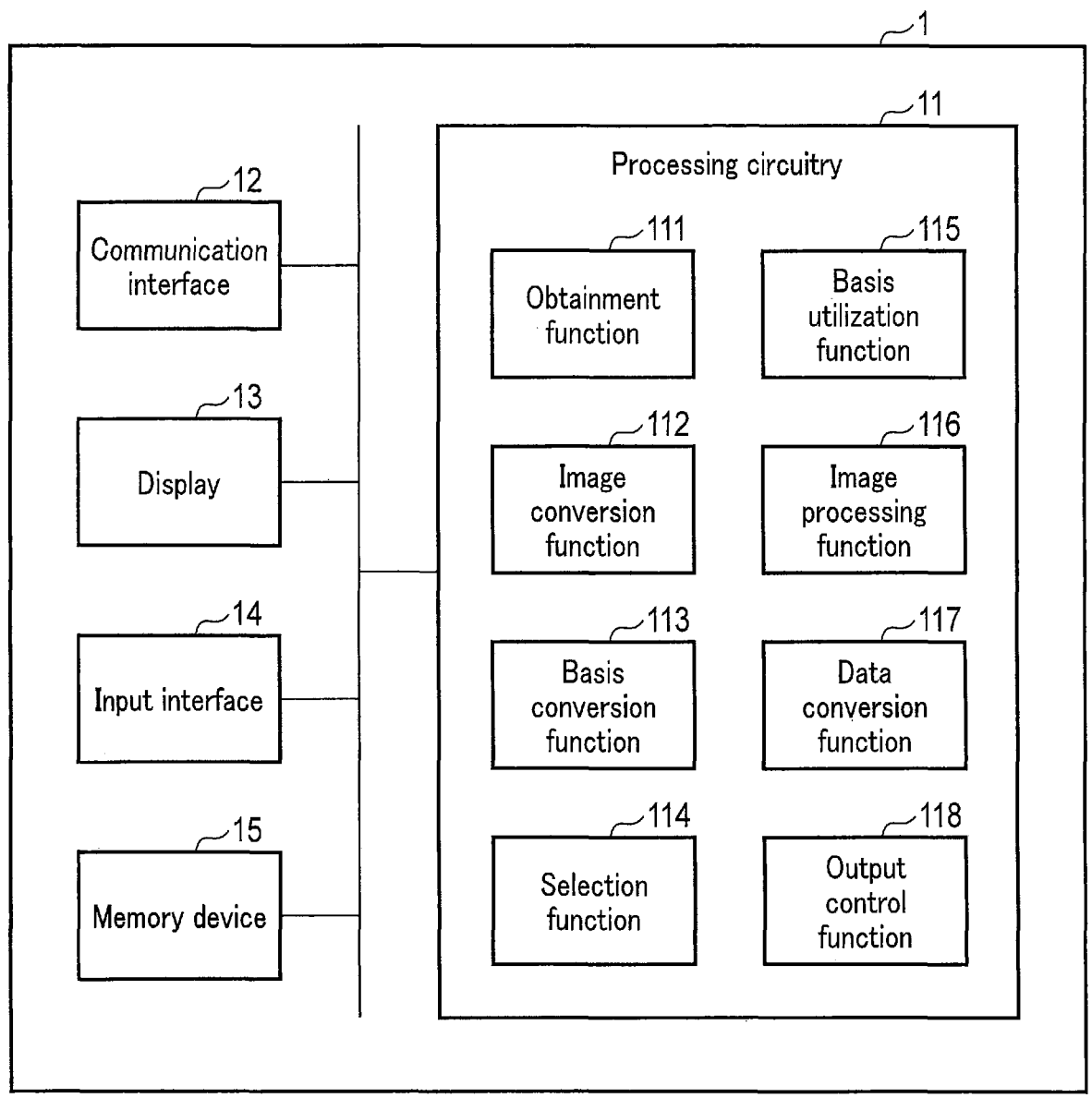
FIG. 1 shows a configuration example of an information processing apparatus according to the present embodiment.

According to an embodiment, an information processing apparatus includes processing circuitry. The processing circuitry calculates a plurality of bases by performing a basis conversion on signal data. The processing circuitry selects one or more specific bases with contribution rates lower than a reference from among the bases. The processing circuitry executes data processing utilizing the specific bases.

An embodiment of the information processing apparatus and method will be described in detail below with reference to the accompanying drawings.

The information processing apparatus according to the present embodiment is a computer which processes various types of digitalized information. Information to be processed is image data acquired by a medical apparatus or an inspection apparatus. The medical apparatus is a medical image diagnostic apparatus which generates image data for medical use. For example, the medical apparatus may be a single-modality apparatus, such as an X-ray computed tomography apparatus (X-ray CT apparatus), a magnetic resonance imaging apparatus (MRI apparatus), an X-ray diagnostic apparatus, a positron emission tomography (PET) apparatus, a single photon emission CT (SPECT) apparatus, an ultrasound diagnostic apparatus, an optical interference tomography apparatus (fundus camera), or an optical ultrasound diagnostic apparatus, or a composite-modality apparatus, such as a PET/CT apparatus, a SPECT/CT apparatus, a PET/MRI apparatus, or a SPECT/MRI apparatus. Alternatively, the medical apparatus may be an optical camera apparatus used accessorily with a medical image diagnostic apparatus, or an optical camera apparatus attached to a catheter. The inspection apparatus is an image generation apparatus which generates image data for inspection use, not for medical use. For example, the inspection apparatus may be an X-ray inspection apparatus, an optical camera apparatus, or a radar measurement apparatus.

When the medical image diagnostic apparatus is an X-ray CT apparatus, a gantry of the X-ray CT apparatus applies X-rays to a subject while rotating an X-ray tube and an X-ray detector around the subject, and detects X-rays that have passed through the subject with the X-ray detector. The X-ray detector generates an electric signal having a peak value corresponding to the detected X-ray dose. The electric signal is subjected to signal processing, such as A/D conversion, by data acquisition circuitry. The A/D converted electric signal is referred to as projection data or sinogram data. A console generates a CT image based on the projection data or sinogram data. The projection data and sinogram data are types of raw data. The projection data, sinogram data, and CT image are types of image data.

When the medical image diagnostic apparatus is an MRI apparatus, a gantry of the MRI apparatus repeats application of a gradient magnetic field via a gradient magnetic field coil and application of an RF pulse via a transmitter coil, under application of a static magnetic field via a static magnetic field magnet. An MR signal is released from the subject in response to the application of the RF pulse. The released MR signal is received via a receiver coil. The received MR signal is subjected to signal processing, such as A/D conversion, by reception circuitry. The A/D converted MR signal is referred to as k-space data. A console generates an MR image based on the k-space data. The k-space data is a type of raw data. The k-space data and MR image are types of image data.

When the medical image diagnostic apparatus is an ultrasound diagnostic apparatus, an ultrasound probe of the ultrasonic diagnostic apparatus transmits ultrasonic beams from a plurality of ultrasound transducers into a subject body, and receives ultrasound reflected from the subject body via the ultrasound transducers. The ultrasound transducers each generate an electric signal having a peak value corresponding to the sound pressure of the received ultrasound. The electric signal is subjected to A/D conversion by an A/D converter provided in the ultrasound probe or the like. The A/D converted electric signal is referred to as echo data. The ultrasound diagnostic apparatus generates an ultrasound image based on the echo data. The echo data is a type of raw data. The echo data and ultrasound image are types of image data.

When the medical image diagnostic apparatus is a PET apparatus, a gantry of the PET apparatus simultaneously measures by coincidence circuitry a pair of 511 keV gamma rays, which are generated due to annihilation of positrons generated from radionuclides accumulated in a subject and electrons around the radionuclides, thereby generating digital data having digital values indicative of the energy value and detection position of the pair of gamma rays. The digital data is referred to as coincidence data or sinogram data. A console generates a PET image based on the coincidence data or sinogram data. The coincidence data and sinogram data are types of raw data. The coincidence data, sinogram data, and PET image are types of image data.

When the medical image diagnostic apparatus is an X-ray diagnostic apparatus, the X-ray diagnostic apparatus generates X-rays from an X-ray tube provided in a C-arm. An X-ray detector, such as a flat panel display (FPD), provided in the C-arm or separately from the C-arm receives X-rays generated by the X-ray tube and having passed through a subject. The X-ray detector generates an electric signal having a peak value corresponding to the detected X-ray dose, and performs signal processing, such as A/D conversion, on the electric signal. The A/D converted electric signal is referred to as projection data or an X-ray image. In the case of a cone-beam CT or the like, the projection data or X-ray image is also used as raw data. The projection data and X-ray image are types of image data.

The raw data according to the present embodiment is a generic term for data that can be converted into an image. The raw data according to the present embodiment is not limited to original raw data acquired by a medical image diagnostic apparatus. For example, the raw data may be computational raw data that is generated by performing inverse conversion processing on a medical image. When raw data is acquired by an X-ray CT apparatus, the inverse conversion processing is, for example, forward projection processing. When raw data is acquired by an MRI apparatus, the inverse conversion processing is, for example, Fourier transform processing. The raw data according to the present embodiment may also be hybrid data that is generated by performing an image conversion on raw data while leaving at least one dimension unconverted among all dimensions defining the raw data. For example, when the raw data is three-dimensional raw data, hybrid data may be that generated by performing an image conversion on the raw data with respect to only one or two axes. As an example, in magnetic resonance imaging, hybrid data generated by performing a Fourier transform on three-dimensional k-space data with respect to only the readout direction is known. Such hybrid data belongs to the category of raw data according to the present embodiment.

FIG. 1 shows a configuration example of an information processing apparatus 1 according to the present embodiment. The information processing apparatus 1 may be a computer included in a medical apparatus or an inspection apparatus, or a computer separate therefrom.

As shown in FIG. 1, the information processing apparatus 1 includes processing circuitry 11, a communication interface 12, a display 13, an input interface 14, and a memory device 15.

The processing circuitry 11 includes a processor, such as a central processing unit (CPU). By activating various programs installed in the memory device 15 or the like, the processor implements an obtainment function 111, an image conversion function 112, a basis conversion function 113, a selection function 114, a basis utilization function 115, an image processing function 116, a data conversion function 117, an output control function 118, and the like. The functions 111 to 118 are not necessarily implemented by a single processing circuit. A plurality of independent processors may be combined into processing circuitry, and execute programs to implement the respective functions 111 to 118.

Through implementation of the obtainment function 111, the processing circuitry 11 obtains image data on a subject. The processing circuitry 11 may obtain the image data from a medical apparatus or an inspection apparatus via the communication interface 12, or from the memory device 15. As mentioned above, image data is a generic term for raw data and an image based on the raw data. The processing circuitry 11 may obtain raw data or an image.

Through implementation of the image conversion function 112, the processing circuitry 11 performs an image conversion on raw data to generate an image. The image conversion executed by the image conversion function 112 is an image conversion that does not utilize the basis selected by the selection function 114 to be described later. As a method of the image conversion from raw data to an image, analytical reconstruction, iterative reconstruction, machine learning reconstruction, and the like can be utilized. Examples of analytical reconstruction for MR image reconstruction include a Fourier transform and an inverse Fourier transform. Examples of analytical reconstruction for CT image reconstruction include filtered back projection (FBP), convolution back projection (CBP), and their applications. Examples of iterative reconstruction include expectation maximization (EM), an algebraic reconstruction technique (ART), and their applications. Machine learning reconstruction is a reconstruction method performed by replacing the entirety or part of an analytical reconstruction or iterative reconstruction with a neural network. As a method of the machine learning reconstruction, for example, iterative reconstruction incorporating a machine learning model that performs denoising is known. Alternatively, the machine learning reconstruction may be performed by a machine learning model that infers an image from raw data. As a method of the image conversion, a reconstruction method such as compressed sensing or parallel imaging reconstruction in magnetic resonance imaging may also be used. Hereinafter, an image generated by the image conversion function 112 will be referred to as a converted image.

Through implementation of the basis conversion function 113, the processing circuitry 11 performs a basis conversion on image data to calculate a plurality of bases. The processing circuitry 11 performs a basis conversion on image data to calculate the number of bases corresponding to the number of dimensions of the image data. As the basis conversion according to the present embodiment, for example, a basis conversion used for dimension reduction or dimension compression may be used. As a method of the basis conversion, for example, a principal component analysis (PCA), singular value decomposition, an independent component analysis, or an encoder/decoder of an encoder/decoder network can be used. The principal component analysis is also called Karhunen-Loeve (KL) expansion.

Through implementation of the selection function 114, the processing circuitry 11 selects one or more specific bases with contribution rates lower than a reference from among the bases calculated by the basis conversion function 113. In other words, the specific bases are bases other than the bases with contribution rates higher than a reference (hereinafter referred to as principle bases) among the bases calculated by the basis conversion function 113. In ordinary dimension compression or the like, principle bases are used as bases that approximate compression target data, and specific bases are evaluated as null in the dimension compression or the like and are rejected. Hereinafter, the specific bases will be referred to as null bases. The number of null bases may be any number larger than or equal to one and smaller than the number of bases calculated by the basis conversion function 113.

Through implementation of the basis utilization function 115, the processing circuitry 11 executes data processing using the null basis selected by the selection function 114. The data processing may be any processing utilizing a null basis and, for example, image conversion or image recognition is suitable therefor. When image conversion is performed, the processing circuitry 11 generates an image by performing an image conversion on the raw data using a space spanned by the null basis (hereinafter referred to as a null space) as a constraint condition. In other words, the processing circuitry 11 generates the image from the raw data so that a constraint condition on the projection amount to the null basis is met. When image recognition is performed, the processing circuitry 11 internally calculates a time-series feature amount sequence by, for example, performing an image conversion on raw data, using the null space as a constraint condition, and converts the calculated time-series feature amount sequence into a recognition result. The feature amount sequence is data which has the same volume as time-series images (corresponding to one channel in the case of grayscale images) and which is constituted by a plurality of channels (for example, 32 channels). The recognition result is a classification value such as a probability of each of a plurality of classes separately specified. The feature amount sequence is an example of image data. Hereinafter, an image generated by the basis utilization function 115 will be referred to as an output image.

Through implementation of the image processing function 116, the processing circuitry 11 performs image processing on the converted image or output image. As the image processing performed by the image processing function 116, for example, image processing for image quality improvement, such as noise reduction processing or smoothing processing, is adopted. However, the image processing performed by the image processing function 116 is not limited to this, and conversion processing into a display image, such as volume rendering, surface volume rendering, pixel value projection, multi-planer reconstruction (MPR), or curved MPR (CPR), may be performed. In addition, as the image processing, display processing, such as gray scale processing or scaling, or image analysis processing may be performed.

Through implementation of the data conversion function 117, the processing circuitry 11 performs a data conversion on various images to generate raw data. The data conversion is processing to perform a reverse process of the image conversion executed by the image conversion function 112.

Through implementation of the output control function 118, the processing circuitry 11 outputs various types of information. For example, the processing circuitry 11 causes the display 13 to display the various types of information or transmit the various types of information to another computer or the like via the communication interface 12.

The communication interface 12 is an interface connecting the information processing apparatus 1 with a medical apparatus, an inspection apparatus, a workstation, a picture archiving and communication system (PACS), a hospital information system (HIS), a radiology information system (RIS), or the like via a local area network (LAN) or the like. The communication interface 12 transmits and receives various types of information to and from the connected apparatus.

The display 13 displays various types of information in accordance with the display control function 118 of the processing circuitry 11. As the display 13, a liquid crystal display (LCD), a cathode ray tube (CRT) display, an organic electroluminescence display (OELD), a plasma display, or any other display can be used as appropriate. Alternatively, the display 13 may be a projector.

The input interface 14 receives various input operations from a user, converts a received input operation into an electric signal, and outputs the electric signal to the processing circuitry 11. Specifically, the input interface 14 is connected to an input device, such as a mouse, a keyboard, a trackball, a switch, a button, a joystick, a touch pad, or a touch panel display. The input interface 14 outputs to the processing circuitry 11 an electric signal corresponding to an input operation on the input device. The input device connected to the input interface 14 may be an input device provided in another computer connected via a network or the like. The input interface 14 may also be a voice recognition device which receives a voice signal acquired via a microphone and converts the voice signal into an instruction signal.

The memory device 15 is a memory device which stores various types of information, such as a read only memory (ROM), a random access memory (RAM), a hard disk drive (HDD), a solid state drive (SSD), or an integrated circuit memory device. The memory device 15 stores, for example, image data, various programs, and the like. Instead of being the above-described memory device, the memory device 15 may be a driver that writes and reads various types of information to and from a semiconductor memory device or a portable storage medium, such as a compact disc (CD), a digital versatile disc (DVD), or a flash memory, or the like. The memory device 15 may be provided in another computer connected to the information processing apparatus 1 via a network.

Hereinafter, a flow of a series of processes relating to image reconstruction using a null space as a constraint condition by the information processing apparatus 1 according to the present embodiment will be described.

Figure 2:
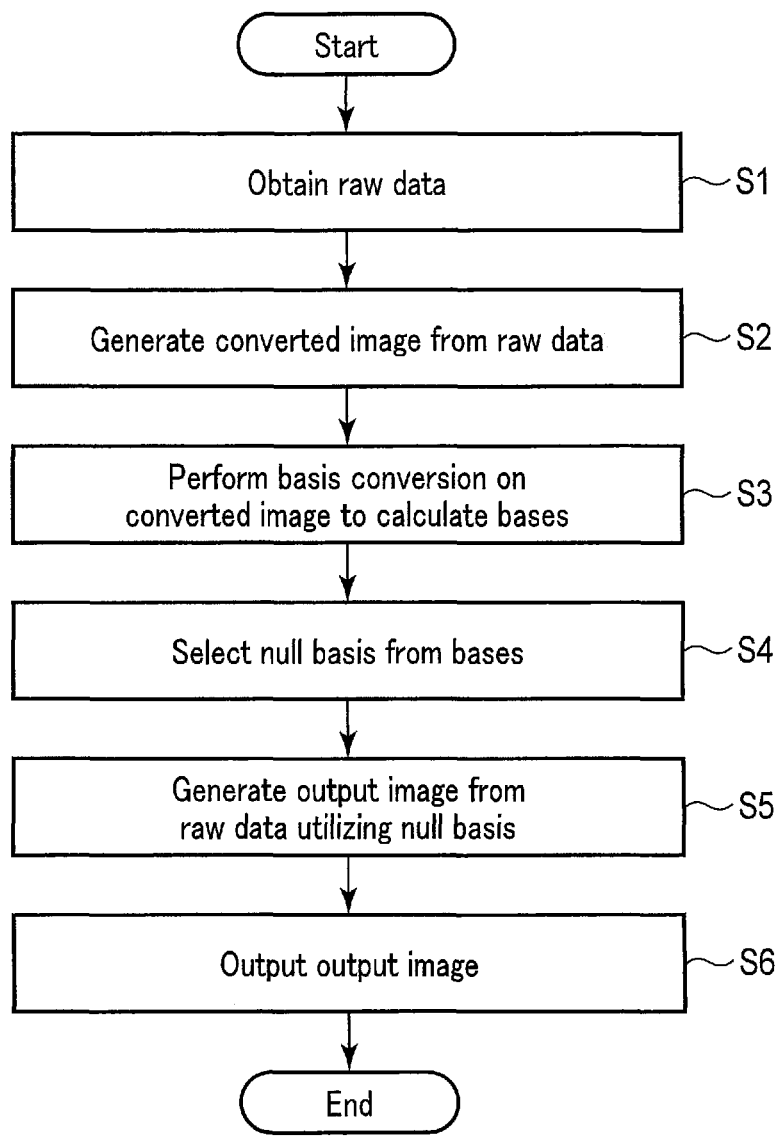
FIG. 2 shows a flow of a series of processes relating to null-space-constraint reconstruction by the information processing apparatus according to the present embodiment.

FIG. 2 shows a flow of a series of processes relating to null-space-constraint reconstruction by the information processing apparatus 1 according to the present embodiment. As shown in FIG. 2, the processing circuitry 11 first obtains raw data (step S1). In step S1, the processing circuitry 11 obtains raw data generated by imaging a subject with a medical apparatus or an inspection apparatus.

After step S1, the processing circuitry 11 generates a converted image from the raw data obtained in step S1, through implementation of the image conversion function 112 (step S2). In step S2, the processing circuitry 11 may generate a converted image from the raw data using any image conversion method described above. The converted image may be a two-dimensional image, a three-dimensional image, or a higher dimensional image.

After step S2, the processing circuitry 11 calculates a plurality of bases by performing a basis conversion on the converted image generated in step S2, through implementation of the basis conversion function 113 (step S3). After step S3, the processing circuitry 11 selects a null basis from the bases calculated in step S3, through implementation of the selection function 114 (step S4).

The processes of steps S3 and S4 are now specifically described. The basis conversion may be performed by, for example, a principal component analysis, singular value decomposition, an independent component analysis, or an encoder of an encoder/decoder network, which is used for dimension reduction or dimension compression; however, let us assume that a principal component analysis (PCA) is used for the basis conversion in order to provide a specific explanation.

In step S3, the processing circuitry 11 first calculates the number of eigenvalues corresponding to the number of dimensions of the converted image and eigenvectors corresponding to the respective eigenvalues. Specifically, the processing circuitry 11 calculates a covariance matrix of the converted image and solves an eigen equation of the covariance matrix to calculate the number of eigenvalues and the number of eigenvectors corresponding to the number of dimensions of the converted image. The eigenvalue corresponds to variance of the converted image. The eigenvector is an example of the basis. The basis calculated by a principal component analysis in the present embodiment may be referred to as a PCA basis. The PCA basis is calculated as a linear basis.

Then, in step S4, the processing circuitry 11 selects, as a null basis, an eigenvector with a contribution rate lower than a reference from among the eigenvectors (PCA bases) calculated in step S3. Specifically, the processing circuitry 11 first calculates the contribution rates of the respective eigenvectors calculated in step S3. The contribution rate is an index that evaluates the degree to which the eigenvector represents all information included in the converted image in a distinguishable manner. The contribution rate of each eigenvector is defined by, for example, a proportion of the eigenvalue of the eigenvector to the sum of all the eigenvalues of all the eigenvectors. Then, the processing circuitry 11 selects, as a null basis, an eigenvector with a contribution rate lower than a reference. The reference may be a threshold or a proportion of the contribution rate, or another reference. For example, the processing circuitry 11 may select, as null bases, eigenvectors with contribution rates lower than or equal to a threshold, eigenvectors ranked lower than a designated rank from the top in contribution rate, or eigenvectors ranked in a designated rank range from the bottom in contribution rate. As the null basis (bases), one eigenvector or a plurality of eigenvectors may be selected. The space spanned by one or more null bases is a null space. In the present embodiment, a principle basis with a contribution rate higher than the reference is rejected.

The method of selecting a null basis is not limited to the above-described method. For example, the processing circuitry 11 may select, as a null basis, an eigenvector of an eigenvalue smaller than a reference while regarding an eigenvalue as the contribution rate of the eigenvector. The method of the basis conversion is not limited to the above-described method. For example, the processing circuitry 11 may use, as the basis conversion, a Fourier transform or a discrete cosine transform, which are used for data compression of the converted image.

After step S4, the processing circuitry 11 generates an output image from raw data by utilizing the null basis selected in step S4, through implementation of the basis utilization function 115 (step S5). In step S5, the processing circuitry 11 generates an output image by performing an image conversion on the raw data obtained in step S1 using the null space spanned by the null basis. Specifically, the processing circuitry 11 performs multiple times an update operation to make an error function, which includes a data consistency term based on raw data and computational raw data based on an updated image and a projection amount of the updated image to each null basis, relatively small to generate an output image from the raw data. The term relating to the projection amount of the updated image to each null basis is referred to as a constraint term. The projection amounts of the updated image to the respective null bases means the projection amount of the updated image to the null space. In the present embodiment, a principal component analysis is performed on the converted image; therefore, the null space is applied in the image space. Here, the processing circuitry 11 minimizes the error function under a constraint condition wherein the constraint term is equal to zero or not more than a predetermined value. In other words, the processing circuitry 11 generates an output image from raw data under a constraint condition wherein the projection amount of the updated image to the null space is equal to zero or is noise.

Specifically, the processing circuitry 11 minimizes the error function EI(x) shown in the following equation (1) to generate an output image:

$$EI(x) = \|FSx - y\|_2^2 + \lambda \|Rx\|_2^2 \qquad (1)$$

As shown in equation (1), the error function EI(x) is defined by the sum of a data consistency term $\|FSx-y\|2^2$ and a constraint term $\lambda\|Rx\|_2^2$. The data consistency term $\|FSx-y\|_2^2$ is defined by a norm of the difference between computational raw data FSx and raw data y. The computational raw data FSx is defined by an inverse image conversion (data conversion) F of the image x and a sensitivity S. The constraint term $\lambda\|Rx\|_2^2$ is defined by a product of the eigenvalue λ and the norm of the projection amount Rx of the image x to the null space R. As the norm, for example, an L2 norm is used. The norm is not limited to an L2 norm, and another norm such as an L1 norm may be used.

The processing circuitry 11 determines a current image that satisfies both of the constraint condition of the constraint term $\lambda\|Rx\|_2^2$ and the minimization condition of the error function EI(x) while sequentially changing the pixel value of each pixel of the current image. The initial image may be a converted image generated by performing an image conversion on raw data or an image with any pixel value distribution. The constraint condition is a condition for constraining the projection amount Rx of the image x to the null space R to be zero. Since the null space R is a space spanned by a null basis with a relatively low contribution rate, the projection amount Rx of the correct image is considered to be zero or to be noise. Specifically, the constraint condition is that the constraint term $\lambda\|Rx\|_2^2$ be zero or not more than a threshold. The threshold is set to a small value close to zero. The minimization condition may be that the error function EI(x) be zero or not more than a threshold, or may be the number of updates. An updated image that satisfies both of the constraint condition and the minimization condition is output as an output image.

The constraint condition may be loosened. The error function EI(x) in this case is set as shown in equation (2) below:

$$EI(x) = \|FSx - y\|_2^2 + \|WRx\|_2^2 \qquad (2)$$

As shown in equation (2), the eigenvalue A is replaced with a weighting matrix W. Each matrix element of the weighting matrix W may be set to a smaller value as the acceptable error becomes larger. For example, each matrix element of the weighting matrix W may be set to, for example, the reciprocal of the square root of the eigenvalue.

After step S5, the processing circuitry 11 outputs the output image generated in step S5, through implementation of the output control function 118 (step S6). In step S6, the processing circuitry 11, for example, causes the display 13 to display the output image, store the output image in the memory device 15, or transmit the output image to another computer via the communication interface 12.

A series of processes relating to null-space-constraint reconstruction is thereby completed.

The processing flow shown in FIG. 2 is an example, and the present embodiment is not limited to this. For example, the processing circuitry 11 may perform a basis conversion on raw data in step S3. In this case, the null space may be applied in the raw data space instead of the image space in the null-space-constraint reconstruction. For example, the error function ED(x) is expressed as shown in equation (3) below:

$$ED(x) = \|FSx - y\|_2^2 + \lambda\|RFx\|_2^2 \qquad (3)$$

As shown in equation (3), the error function ED(x) is defined by the sum of a data consistency term $\|FSx-y\|_2^2$ and a constraint term $\lambda\|RFx\|_2^2$. As in equation (1), the data consistency term $\|FSx-y\|_2^2$ is defined by a norm of the difference between computational raw data FSx and raw data y. The constraint term $\lambda\|RFx\|_2^2$ is defined by a product of the eigenvalue λ and a norm of the projection amount Rx of the computational raw data Fx based on the updated image x to the null space R. As the norm, for example, an L2 norm is used. The computational raw data Fx is calculated by performing an inverse image conversion (data conversion) F on the updated image x. In this case, the processing circuitry 11 may determine an updated image that satisfies both of the constraint condition of the constraint term $\lambda\|RFx\|_2^2$ and the minimization condition of the error function ED(x) while sequentially changing the pixel value of each pixel of the updated image. Also in this example, instead of λ in the error function ED(x), the diagonal weighting matrix W shown in equation (2) may be used.

According to the above explanation, the processing circuitry 11 performs a basis conversion on image data to calculate a plurality of bases, through implementation of the basis conversion function 113. However, the data to be subjected to the basis conversion is not limited to image data. The processing circuitry 11 performs a basis conversion on signal data to calculate a plurality of bases. The signal data refers to data, such as image data, which can be processed by a computer. Examples of the signal data, other than image data, include waveform data, which is series data of signal strength values. The waveform data may be time-series data, frequency-series data, or any other physical-quantity-series data of signal strength values. The data processing by the basis utilization function 115 is described above as image conversion or image recognition. However, the data processing is not limited to these and may be, for example, noise reduction (denoising) of signal data.

According to the above-described embodiment, the information processing apparatus 1 includes processing circuitry 11. The processing circuitry 11 performs a basis conversion on signal data to calculate a plurality of bases. The processing circuitry 11 selects a null basis with a contribution rate lower than a reference from among the bases. The processing circuitry 11 executes data processing utilizing the null basis.

The above-described configuration can provide new data processing utilizing a null basis which has been rejected in low-rank approximation or the like based on a principal component analysis or singular value decomposition.

Next, examples of the information processing apparatus 1 according to the present embodiment will be described. In the following examples, the information processing apparatus 1 is assumed to process image data generated by a magnetic resonance imaging apparatus as long as there is no particular description to the contrary. As the method of the basis conversion, a principal component analysis (PCA) is assumed to be used. The data processing by the basis utilization function 115 is assumed to be null-space-constraint reconstruction using a null space as a constraint condition. The various images may be a two-dimensional image, a three-dimensional image, or a higher dimensional image, but is assumed to be a two-dimensional image for example.

First Example

The processing circuitry 11 according to a first example performs, through the basis conversion function 113, a basis conversion with respect to the temporal axis direction on image data. The image data to be subjected to the basis conversion is assumed to be time-series images. Time-series images are known to be highly correlated with respect to the temporal axis direction. Thinned-out reconstruction is performed by utilizing this property. Even if each image has a low signal-to-noise ratio (SNR), high SNR reconstruction can be achieved.

Figure 3:
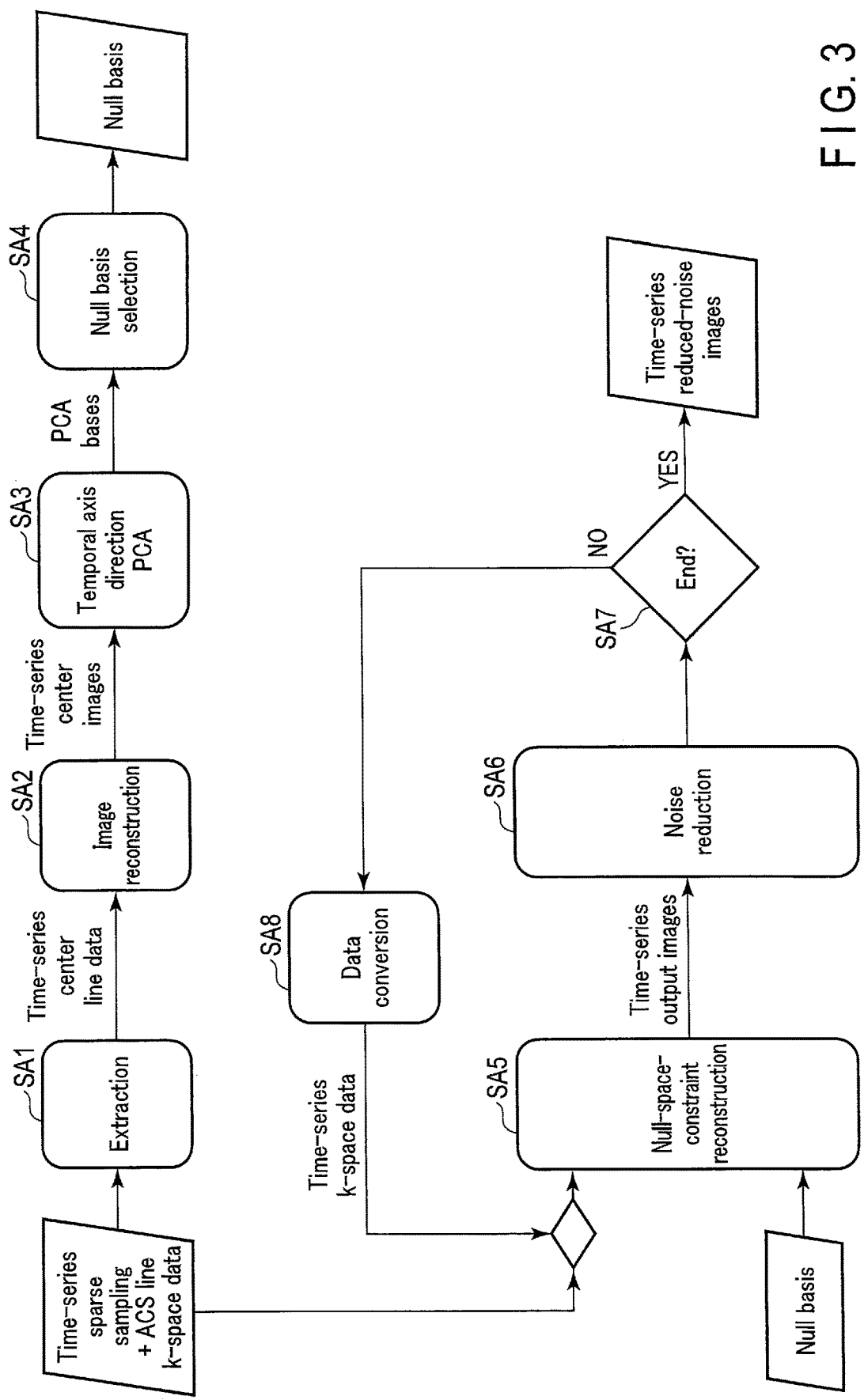
FIG. 3 schematically shows a processing example including null-space-constraint reconstruction by the information processing apparatus according to a first example.

FIG. 3 schematically shows a processing example including null-space-constraint reconstruction by the information processing apparatus 1 according to the first example. As shown in FIG. 3, the processing circuitry 11 first obtains time-series sparse sampling+ACS line k-space data through implementation of the obtainment function 111. The time-series sparse sampling+ACS line k-space data is an example of time-series k-space data. The time-series sparse sampling+ACS line k-space data is acquired by a magnetic resonance imaging apparatus executing sparse sampling acquisition accompanied by ACS line acquisition, and is transferred from the magnetic resonance imaging apparatus to the information processing apparatus 1. The sparse sampling acquisition accompanied by ACS line acquisition is a data acquisition method including sparse sampling acquisition for acquiring data by thinning out the k-space lines in accordance with a set acceleration rate and data acquisition of k-space lines (ACS lines) in a center part of the k-space in the phase encoding direction. The sparse sampling acquisition accompanied by ACS line acquisition is an application of a k-space method, which is a method of parallel imaging, and generalized auto-calibrating partially parallel acquisition (GRAPPA) is known as an example thereof.

Figure 4:
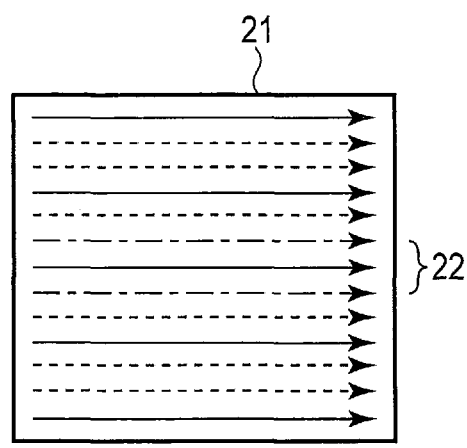
FIG. 4 is a schematic view of sparse sampling+ACS line k-space data used in the first example.

FIG. 4 is a schematic view of sparse sampling+ACS line k-space data 21. In FIG. 4, the solid-line and dashed-dotted-line arrows indicate k-space lines for which data was acquired by sparse sampling acquisition accompanied by ACS line acquisition, and the dotted-line arrows indicate thinned-out k-space lines for which data was not acquired. The dashed-dotted-line arrows indicate k-space lines (ACS lines) for which data was acquired by ACS line acquisition, and the solid-line arrows indicate k-space lines for which data was acquired by sparse sampling acquisition. As shown in FIG. 4, the sparse sampling+ACS line k-space data 21 includes k-space data of the k-space lines for which data was acquired by sparse sampling acquisition and k-space data of the ACS lines. Of the ACS lines and the k-space lines for which data was acquired by sparse sampling acquisition, k-space lines in a center part in the phase encoding direction will be referred to "center lines", and k-space data of the center lines will be referred to as center line data 22. The range of the center part is not particularly limited, and may be set to a range including any number of k-space lines. As the center line data 22, only k-space data of the ADS lines in the center part or only k-space data of the k-space lines for which data was acquired by sparse sampling acquisition may be extracted. The ACS lines and k-space lines shown in FIG. 4 are mere examples, and the number, thinning rate, etc. of the k-space lines are not particularly limited in this example.

As shown in FIG. 3, upon acquisition of the time-series sparse sampling+ACS line k-space data, the processing circuitry 11 extracts time-series center line data from the time-series sparse sampling+ACS line k-space data through implementation of the obtainment function ill (step SA1).

After step SA1, the processing circuitry 11 performs image reconstruction on the time-series center line data extracted in step SA1 to generate time-series center images through implementation of the image conversion function 112 (step SA2). After step SA2, the processing circuitry 11 performs a principal component analysis with respect to the temporal axis direction on the time-series center images generated in step SA2 to calculate a plurality of PCA bases through implementation of the basis conversion function 113 (step SA3). After step SA3, the processing circuitry 11 selects a null basis from the PCA bases calculated in step SA3, through implementation of the selection function 114 (step SA4). The processes of steps SA3 and SA4 are now specifically described.

FIG. 5 schematically shows the processes of steps SA2 to SA4. As shown in FIG. 5, in step SA2, the processing circuitry 11 first generates time-series center images 23 by performing image reconstruction on the time-series center line data extracted in step SA1. In the case of FIG. 5, for example, center images 23 of 16 frames (time points) are generated. The matrix size of each center image 23 is not particularly limited. The number of pixels of each center image 23 is assumed to be K (where K is an integer). The time-series center images 23 are arranged along the temporal axis in a three-dimensional space (hereinafter referred to as an xy-t space) defined by two dimensions of image axes and one dimension of a temporal axis. The two dimensions of image axes are coordinate axes defining the position of each pixel of the image. The temporal axis is a coordinate axis defining the acquisition time of k-space data corresponding to the center image 23. The time-series center images 23 are highly correlated with respect to the temporal axis direction.

As shown in FIG. 5, upon generation of the time-series center images 23, the processing circuitry 11 performs a principal component analysis on the time-series center images 23 arranged in the xy-t space. Specifically, the processing circuitry 11 first records the change of the pixel value along the temporal axis for all pixels k of the center images 23 (where k is an index of each pixel; $1 \leq k \leq K$). For example, for each pixel k, a vector Vk(t) indicating the change of the pixel value along the temporal axis can be obtained. The number of elements of the vector Vk(t) corresponds to the number of frames, and is equal to 16 in the case of FIG. 5. In this case, the vector Vk(t) is a point in a 16-dimensional space.

As shown in FIG. 5, upon obtainment of the vector Vk(t) indicating the temporal change in the pixel value for all of the K pixels, the processing circuitry 11 performs a principal component analysis on the vectors Vk(t) of the K pixels to calculate the same number of PCA bases Uj (where j is an index of each PCA basis; $1 \leq j \leq K$) as the frames. As shown in FIG. 5, when the number of frames is 16, 16 PCA bases are calculated. Each PCA basis Uj includes the same number of elements uj,k as the frames. For convenience, the indexes of PCA bases are assumed to be assigned in descending order of the eigenvalue or variance value.

As shown in FIG. 5, upon calculation of the PCA bases Uj, the processing circuitry 11 selects, as a null basis Uj, a PCA basis Uj with a contribution rate lower than a reference. For example, when the reference is the third rank from the top in the eigenvalue or variance value, PCA bases U1 to U3 are set as principle bases and rejected, and PCA bases U4 to U16 are set as null bases and selected. As mentioned above, the reference is not limited to the third rank from the top. The processing circuitry 11 stores each principle basis in the memory device 15 after assigning thereto a flag indicating that the PCA basis is a principle basis, and stores each null basis in the memory device 15 after assigning thereto a flag indicating that the PCA basis is a null basis.

After step SA4, the processing circuitry 11 generates time-series output images based on the time-series sparse sampling+ACS line k-space data and the null basis selected in step SA4, through implementation of the basis utilization function 115 (step SA5). Specifically, in step SA5, the processing circuitry 11 generates the output images by performing an image conversion on the time-series sparse sampling+ACS line k-space data using the null space spanned by the null basis selected in step SA4 as a constraint condition. In other words, the processing circuitry 11 minimizes the error function EI(x) exemplified in equation (1) or (2) under the constraint condition that the constraint term is equal to zero or not more than a predetermined value. More specifically, the processing circuitry 11 determines an updated image that satisfies both of the constraint condition of the constraint term $\lambda \|Rx\|_2^2$ and the minimization condition of the error function EI(x) while sequentially changing the pixel value of each pixel of the updated image. The constraint condition and minimization condition may be set in a similar manner to the above. The initial image of the updated image may be a converted image generated by performing an image conversion on raw data or an image with any pixel value distribution. In the case of the first example, in which k-space data acquired by sparse sampling acquisition is used, for example, a non-uniform discrete Fourier transform (NUDFT) is used as the function F in equation (1) or (2).

After step SA5, the processing circuitry 11 performs noise reduction processing on the time-series output images generated in step SA5, through implementation of the image processing function 116 (step SA6). The output images after noise reduction processing in step SA6 will be referred to as reduced-noise images. In step SA6, for the noise reduction processing, the processing circuitry 11 may use a noise reducing filter, a neural network, such as a convolutional neural network for noise reduction, or any other method.

After step SA6, the processing circuitry 11 determines whether or not to terminate the null-space-constraint reconstruction (step SA7). In step SA7, the processing circuitry 11 determines whether or not a termination condition is met. The termination condition may be, for example, that the number of repetitions has reached a predetermined number, that the image quality evaluation index of the SNR of each reduced-noise image is smaller than or equal to a threshold, or any other condition. The processing circuitry 11 determines not to terminate the null-space-constraint reconstruction when the termination condition is not met, and determines to terminate the null-space-constraint reconstruction when the termination condition is met.

When it is determined not to terminate the null-space-constraint reconstruction (No in SA7), the processing circuitry 11 performs a data conversion on the time-series noise-reduced images generated in step SA6 to generate time-series computational k-space data, through implementation of the data conversion function 117 (step SA8). After step SA8, the processing circuitry 11 generates new time-series output images based on the time-series computational k-space data generated in step SA8 and the null basis selected in step SA4 (step SA5), and executes noise reduction processing on the new time-series output images generated in step SA5 (step SA6). Then, the processing circuitry 11 determines again whether or not to terminate the null-space-constraint reconstruction (step SA7). In this manner, the processing circuitry 11 repeats steps SA5 to SA8 until it is determined that the termination condition is met in step SA7.

When it is determined to terminate the null-space-constraint reconstruction (Yes in SA7), the processing circuitry 11 causes the display 13 to display the time-series reduced-noise images generated in step SAG, stores the time-series reduced-noise images in the memory device 15, or transmits the time-series reduced-noise images to another computer via the communication interface 12, through implementation of the output control function 118.

The processing including null-space-constraint reconstruction according to the first example is thereby completed.

FIG. 6 shows output images of First Example (A), Comparative Example (B), and Comparative Example (C). The data condition of the first example is frame number=16, phase encoding number=168, readout number=192, coil number=1 (single coil), and a combination of sampling pattern=k-t4x and ACS line number=32 (acceleration rate=168/66=2.5). The reconstruction condition of First Example (A) is that null-space-constraint reconstruction was used, the top three eigenvectors were rejected, and the remaining 13 eigenvectors were selected as null bases. The output image of First Example (A) is an average image of time-series output images obtained by performing null-space-constraint reconstruction on time-series sparse sampling+ACS line k-space data obtained under the above conditions.

The data condition of Comparative Example (B) is the same as the data condition of First Example (A). The output image of Comparative Example (B) is an average image of time-series output images obtained by performing zero filling on the time-series sparse sampling+ACS line k-space data obtained under the above condition to generate time-series filled k-space data and performing an image conversion (non-null-space-constraint reconstruction) on the time-series filled k-space data. The data condition of Comparative Example (C) is frame number=16, phase encoding number=168, readout number=192, coil number=1 (single coil), and sampling pattern=full sampling. The output image of Comparative Example (C) is an average image of time-series output images obtained by performing an image conversion (non-null-space-constraint reconstruction) on time-series full sampling k-space data obtained under the above condition.

It can be confirmed from FIG. 6 that the output image of First Example (A) has a similar image quality to the output image of Comparative Example (C). Therefore, it can be confirmed that null-space-constraint reconstruction using a null basis obtained by a principal component analysis with respect to the temporal axis direction according to the first example is useful.

The above-described processing including null-space-constraint reconstruction according to the first example is a mere example, and may be modified in various ways. For example, in the above example, the principal component analysis with respect to the temporal axis direction is assumed to be applied to time-series center images based on time-series center line data having a relatively small matrix size to reduce the calculation load of the principal component analysis. However, the principal component analysis with respect to the temporal axis direction may be applied to any converted images as long as they are time-series converted images. For example, the principal component analysis with respect to the temporal axis direction may be applied to time-series converted images based on time-series k-space data acquired by parallel imaging of a real space method, such as sensitivity encoding (SENSE), which does not involve ACS line acquisition. The time-series converted images to which the principal component analysis with respect to the temporal axis direction is applied need not be those at different times aligned in frame number order along the temporal axis, and may be those at different times aligned in an order other than the frame number order. For example, the converted images may be aligned randomly or pseudo-randomly with respect to their frame numbers.

As described above, the processing circuitry 11 according to the first example calculates a plurality of bases by performing a basis conversion with respect to the temporal axis direction on time-series images based on time-series k-space data, selects a null basis with a relatively low contribution rate from among the calculated bases, and generates time-series output images by performing, on the time-series k-space data, null-space-constraint reconstruction using a null space spanned by the null basis as a constraint condition.

According the above configuration, a null space spanned by a null basis derived from a basis conversion with respect to the temporal axis direction is used as a constraint condition; therefore, in the reconstruction process, information with a low temporal correlation included in time-series images is actively lightened, whereas information with a high temporal correlation is passively weighted, relatively. Accordingly, the first example enables reconstruction using information in the temporal axis direction. In addition, since the projection amounts of the time-series images to the null space are strongly presumed to be zero or to be noise, the null-space-constraint reconstruction according to the first example can have a smaller calculation load than low-rank approximation model reconstruction using a principle basis.

Second Example

The processing circuitry 11 according to a second example performs, through the basis conversion function 113, a basis conversion with respect to an image space axis direction on image data. The image data to be subjected to the basis conversion is assumed to be a single image.

Figure 7:
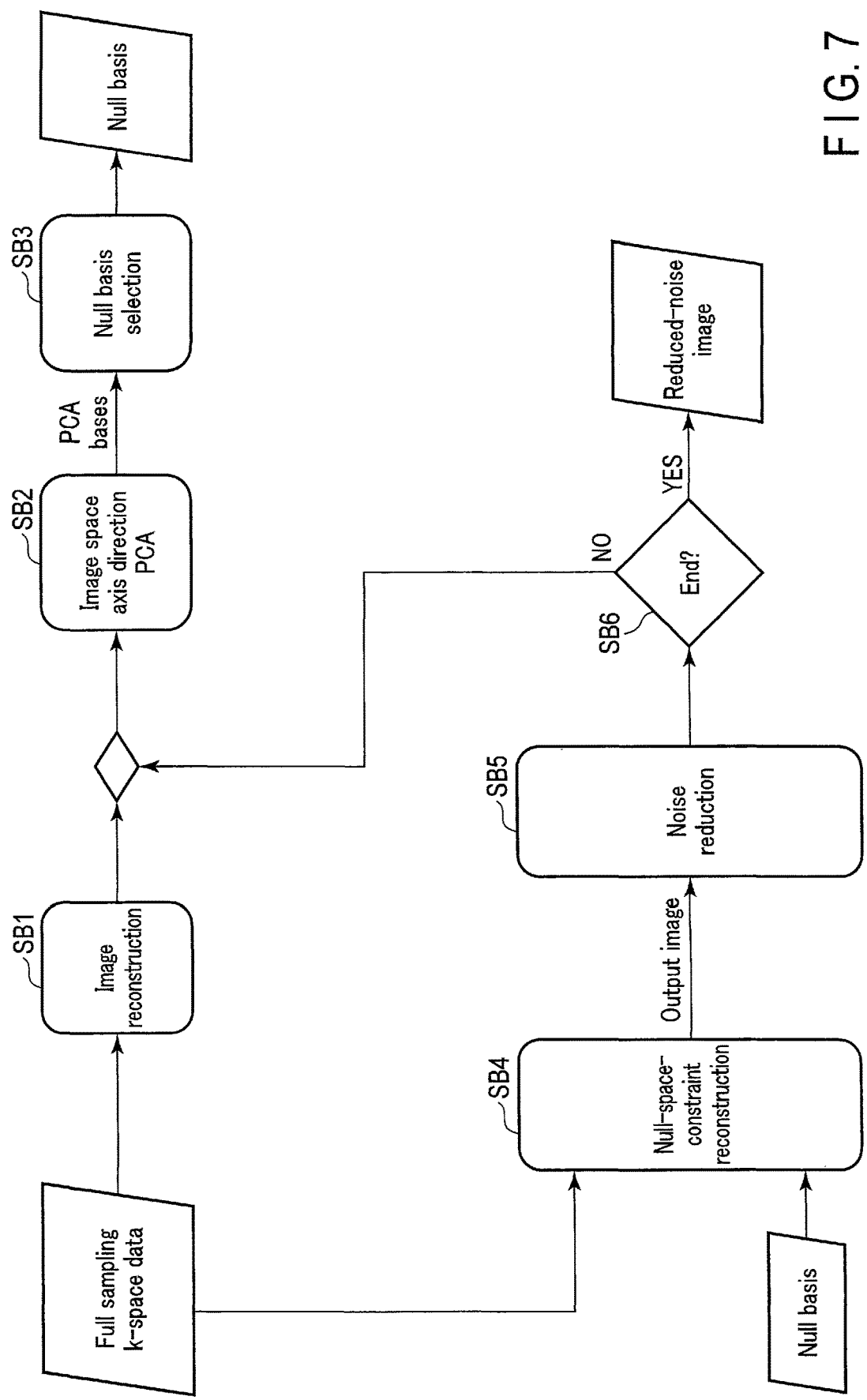
FIG. 7 schematically shows a processing example including null-space-constraint reconstruction by the information processing apparatus according to a second example.

FIG. 7 schematically shows a processing example including null-space-constraint reconstruction by the information processing apparatus 1 according to the second example. As shown in FIG. 7, the processing circuitry 11 first obtains full sampling k-space data through implementation of the obtainment function 111. The full sampling k-space data is acquired by a magnetic resonance imaging apparatus executing full sampling acquisition, and is transferred from the magnetic resonance imaging apparatus to the information processing apparatus 1. The full sampling acquisition is a data acquisition method of acquiring data without thinning the k-space lines.

As shown in FIG. 7, upon acquisition of the full sampling k-space data, the processing circuitry 11 performs image reconstruction on the full sampling k-space data to generate a reconstructed image, through implementation of the image conversion function 112 (step SB1). After step SB1, the processing circuitry 11 performs a principal component analysis with respect to an image space axis direction on the reconstructed image generated in step SB1 to calculate a plurality of PCA bases, through implementation of the basis conversion function 113 (step SB2). After step SB2, the processing circuitry 11 selects a null basis from the PCA bases calculated in step SB2 through implementation of the selection function 114 (step SB3). The processes of steps SB2 and SB3 are now specifically described.

Figure 8:
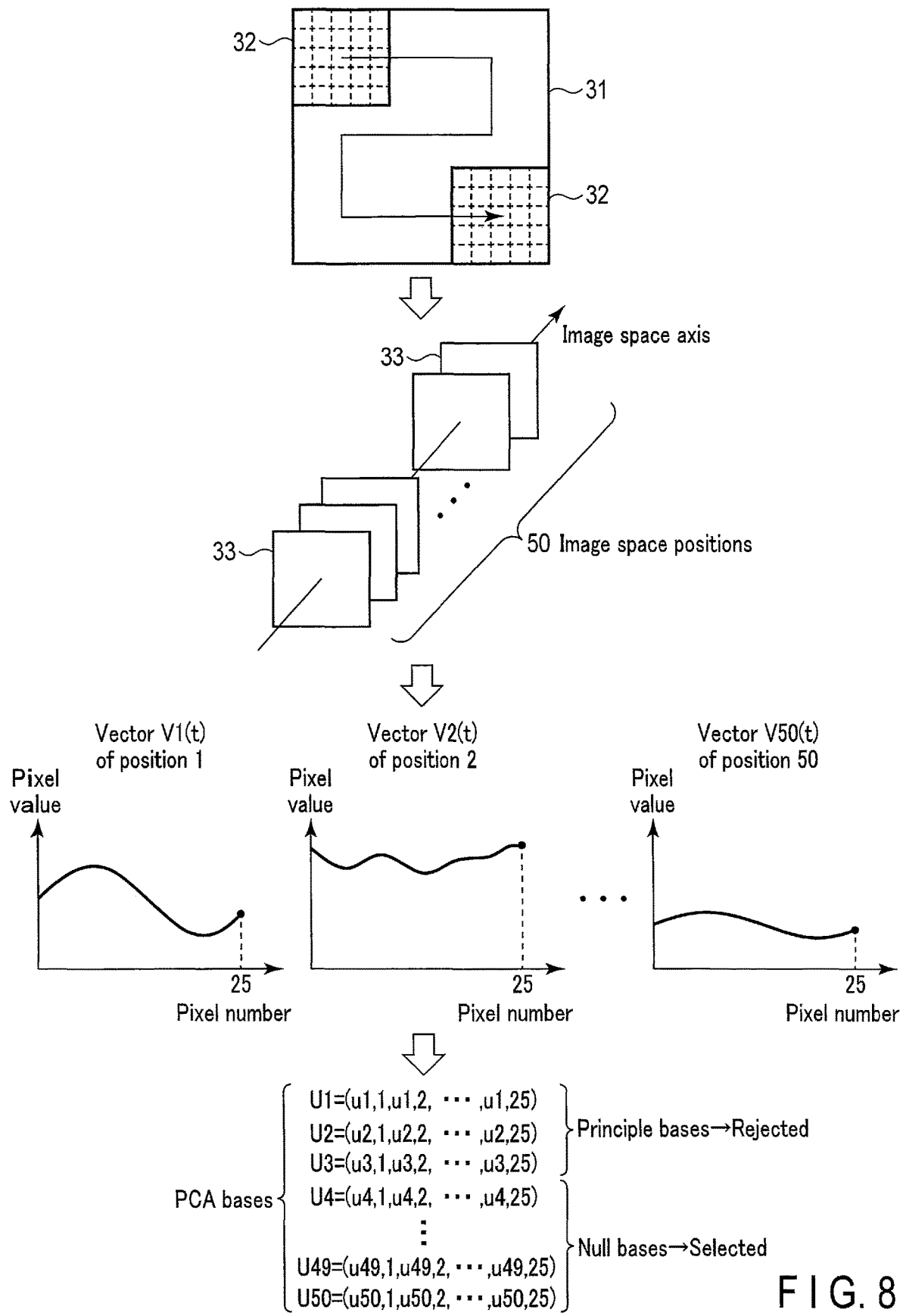
FIG. 8 schematically shows processes of steps SB2 and SB3 in FIG. 7.

FIG. 8 schematically shows the processes of steps SB2 and SB3. As shown in FIG. 8, a reconstructed image 31 is generated based on full sampling k-space data in step SB1. As shown in FIG. 8, the processing circuitry 11 generates, from the reconstructed image 31, a plurality of local images 33 corresponding to a plurality of local areas 32 set at different positions of the reconstructed image 31. Specifically, the processing circuitry 11 sets a local area 32 of a predetermined block size in a corner of the reconstructed image 31, and generates a pixel value distribution in the set local area 32 as a local image 33. The processing circuitry 11 slides the local area 32 over the entire area on the reconstructed image 31. While doing so, the processing circuitry 11 generates a pixel value distribution of the local area 32 as a local image 33 at every slide of a predetermined distance. Accordingly, a plurality of local images 33 corresponding to a plurality of local areas 32 are generated. The local images 33 are arranged along the image space axis in a three-dimensional space (hereinafter referred to as an xy-s space) defined by two dimensions of image axes and one dimension of an image space axis. The image space axis is a coordinate axis defining the position of the local area 32 or local image 33 in the reconstructed image 31. The series of local images 33 are highly correlated with respect to the image space axis direction.

The block size may be any size as long as it is smaller than the matrix size of the reconstructed image 31. For example, when the matrix size of the reconstructed image 31 is 512×512, the block size may be any smaller size, such as 5×5, 7×7, or 11×11. The number of local areas 32 (the number of image space positions) is not particularly limited, either. FIG. 8 shows, as an example, the case where the block size is 5×5, i.e., the number of pixels of the local image 33 is 25, and the number of image space positions is 50. A local area 32 may or may not overlap another local area 32.

As shown in FIG. 8, upon generation of the local images 33, the processing circuitry 11 performs a principal component analysis on the local images 33 arranged in the xy-s space. Specifically, first, pixel values of 5×5 pixels are arranged to generate one 25-dimensional vector for each of all image space positions k (where k is an index of each image space position; $1 \leq k \leq 50$) of the local image 33. For example, for each image space position k, 50 25-dimensional vectors Vk(t) indicating the change in the pixel value along the pixel numbers can be obtained. The number of elements of the vector Vk(t) corresponds to the block size, and is equal to 25 in the case of FIG. 8. In this case, the vector Vk(t) means a point in a 25-dimensional space.

As shown in FIG. 8, upon obtainment of the vector Vk(t) indicating the change in the pixel value along the pixel numbers for all of the 50 image space positions, the processing circuitry 11 performs a principal component analysis on the 50 vectors Vk(t), and calculates the same number of PCA bases Uj (where j is an index of the PCA basis; $1 \leq j \leq 25$) as the block size. As shown in FIG. 8, when the block size is 25, 25 PCA bases are calculated. Each PCA basis Uj includes the same number of elements uj,k as the block size. For convenience, the indexes of PCA bases are assumed to be assigned in descending order of the eigenvalue or variance value.

As shown in FIG. 8, upon calculation of the PCA bases Uj, the processing circuitry 11 selects, as a null basis Uj, a PCA basis Uj with a contribution rate lower than a reference. For example, when the reference is the third rank from the top in the eigenvalue or variance value, PCA bases U1 to U3 are set as principle bases and rejected, and PCA bases U4 to U50 are set as null bases and selected. As mentioned above, the reference is not limited to the third rank from the top. The processing circuitry 11 stores each principle basis in the memory device 15 after assigning thereto a flag indicating that the PCA basis is a principle basis, and stores each null basis in the memory device 15 after assigning thereto a flag indicating that the PCA basis is a null basis. According to the above description, the processing circuitry 11 obtains a vector Vk(t) for each local image (image space position); however, the processing circuitry 11 may obtain a vector Vk(t) for a coupled local image obtained by coupling two or more adjacent local images.

After step SB3, the processing circuitry 11 generates an output image based on the full sampling k-space data and the null basis selected in step SB3, through implementation of the basis utilization function 115 (step SB4). Specifically, in step SB4, the processing circuitry 11 generates an output image by performing an image conversion on the full sampling k-space data using the null space spanned by the null basis selected in step SB3 as a constraint condition. Specifically, the processing circuitry 11 minimizes the error function EI(x) exemplified in equation (1) or (2) under a constraint condition wherein the constraint term is equal to zero or not more than a predetermined value. More specifically, the processing circuitry 11 determines an updated image that satisfies both of the constraint condition of the constraint term $\lambda \|Rx\|_2^2$ and the minimization condition of the error function EI(x) while sequentially changing the pixel value of each pixel of the updated image. The constraint condition and minimization condition may be set in a similar manner to the above-described ones. The initial image of the updated image may be a converted image generated by performing an image conversion on raw data or an image with any pixel value distribution. In the case of the second example, in which k-space data acquired by full sampling acquisition is used, for example, a discrete Fourier transform (DFT) may be used as the function F in equation (1) or (2).

After step SB4, the processing circuitry 11 performs noise reduction processing on the output image generated in step SB4 to generate a reduced-noise image, through implementation of the image processing function 116 (step SB5). The noise reduction processing in step SB5 may be performed in a manner similar to that in step SA6.

After step SB5, the processing circuitry 11 determines whether or not to terminate the null-space-constraint reconstruction (step SB6). In step SB6, the processing circuitry 11 determines whether or not a termination condition is met. The termination condition may be, for example, that the number of repetitions has reached a predetermined number, that the image quality evaluation index of the SNR of the reduced-noise image is smaller than or equal to a threshold, or any other condition. The processing circuitry 11 determines not to terminate the null-space-constraint reconstruction when the termination condition is not met, and determines to terminate the null-space-constraint reconstruction when the termination condition is met.

When it is determined to not terminate the null-space-constraint reconstruction (No in SB6), the processing circuitry 11 performs a principal component analysis with respect to the image space axis direction on the reduced-noise image generated in step SB5 to calculate a plurality of PCA bases (step SB2), selects a null basis from among the PCA bases calculated in step SB2 (step SB3), generates an output image based on the full sampling k-space data and the null basis selected in step SB3 (step SB4), and executes noise reduction processing on the output image generated in step SB4 (step SB5). Then, the processing circuitry 11 determines again whether or not to terminate the null-space-constraint reconstruction (step SB6). In this manner, the processing circuitry 11 repeats steps SB3 to SB6 until it is determined that the termination condition is met in step SB6.

When it is determined to terminate the null-space-constraint reconstruction (Yes in SB6), the processing circuitry 11 causes the display 13 to display the reduced-noise image generated in step SB5, stores the reduced-noise image in the memory device 15, or transmits the reduced-noise image to another computer via the communication interface 12, through implementation of the output control function 118.

The processing including null-space-constraint reconstruction according to the second example is thereby completed.

The above-described processing including null-space-constraint reconstruction according to the second example is a mere example, and may be modified in various ways. For example, image data to be subjected to the basis conversion with respect to the image space axis is described above as being a converted image based on full sampling k-space data, which is expected to have high quality, so that the accuracy in the basis conversion with respect to the image space axis is secured. However, the present example is not limited to this, and the basis conversion may be performed on the converted image based on sparse sampling k-space data or a principal component analysis may be performed on a past image. For example, when null-space-constraint reconstruction is performed on k-space data after contrast enhancement in step SB4, a principal component analysis may be performed on a converted image based on k-space data before contrast enhancement in step S2.

As described above, the processing circuitry 11 according to the second example calculates a plurality of bases by performing a basis conversion with respect to the image space axis direction on a single image, selects a null basis with a relatively low contribution rate from among the calculated bases, and generates an output image by performing, on k-space data, null-space-constraint reconstruction using a null space spanned by the null basis as a constraint condition.

According to the above configuration, a null space spanned by a null basis derived from a basis conversion with respect to the image space axis direction is used as a constraint condition; therefore, in the reconstruction process, information with a low image space correlation included in a single image is actively lightened, whereas information with a high image space correlation is passively weighted, relatively. Accordingly, the second example enables reconstruction using information in the image space axis direction. In addition, since the projection amount of the single image to the null space is strongly presumed to be zero or to be noise, the null-space-constraint reconstruction according to the second example can have a smaller calculation load than low-rank approximation model reconstruction using a principle basis.

Third Example

The processing circuitry 11 according to a third example performs, through the basis conversion function 113, basis conversions with respect to a temporal axis direction and an image space axis direction on image data.

Figure 9:
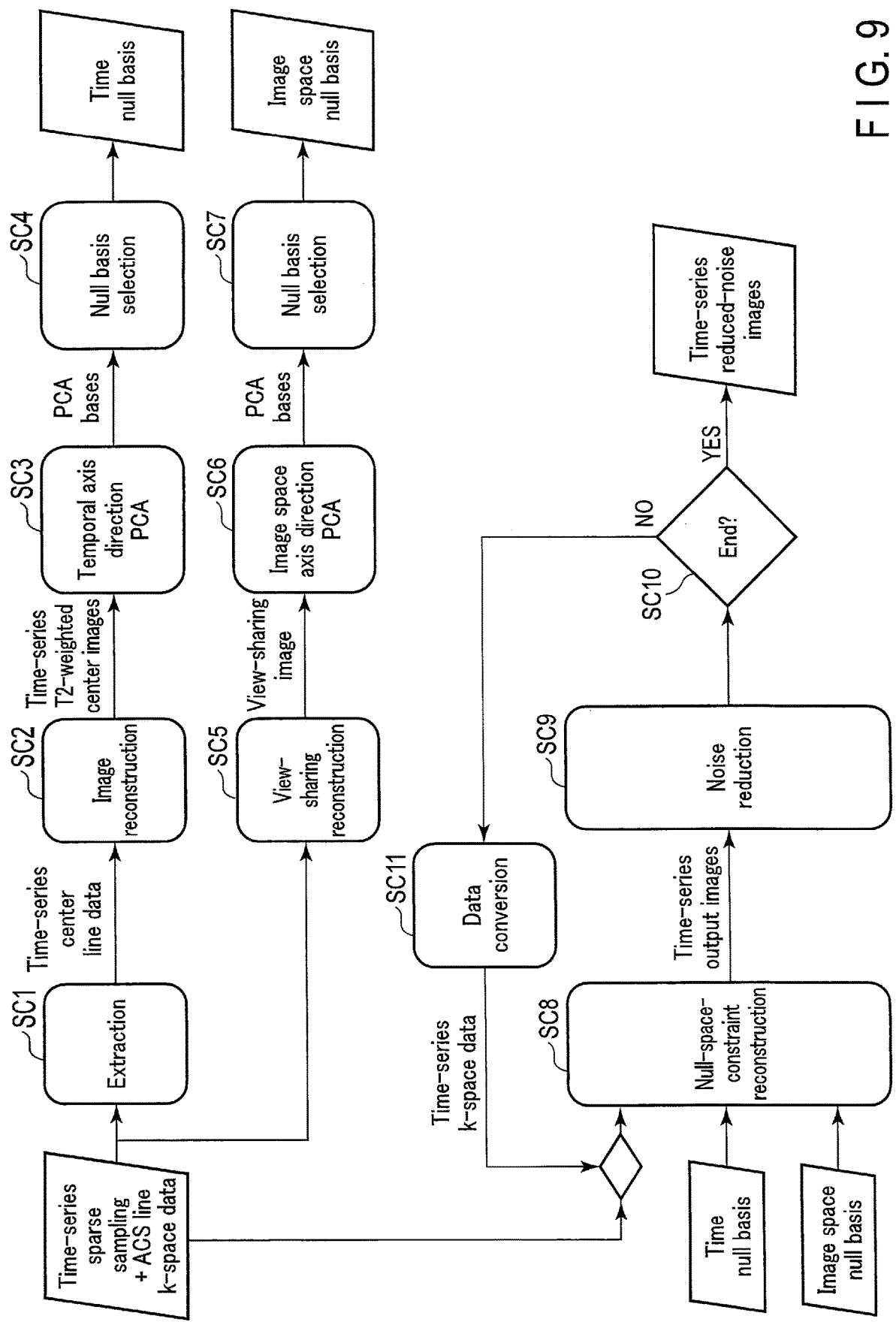
FIG. 9 schematically shows a processing example including null-space-constraint reconstruction by the information processing apparatus according to a third example.

FIG. 9 schematically shows a processing example including null-space-constraint reconstruction by the information processing apparatus 1 according to the third example. As shown in FIG. 9, the processing circuitry 11 first obtains time-series sparse sampling+ACS line k-space data through implementation of the obtainment function 111. The time-series sparse sampling+ACS line k-space data of the third example is the same as the time-series sparse sampling+ACS line k-space data of the first example.

As shown in FIG. 9, the processing circuitry 11 performs both of a basis conversion with respect to the temporal axis direction and a basis conversion with respect to the image space axis direction on the time-series sparse sampling+ACS line k-space data and selects a null basis derived from the basis conversion with respect to the temporal axis direction (hereinafter referred to as a time null basis) and a null basis derived from the basis conversion with respect to the image space axis direction (hereinafter referred to as an image space null basis).

Specifically, as in the first example, the processing circuitry 11 extracts time-series center line data from time-series sparse sampling+ACS line k-space data (step SC1), performs image reconstruction on the time-series center line data to generate time-series center images (step SC2), performs a principal component analysis with respect to the temporal axis on the time-series center images to calculate a plurality of PCA bases (step SC3), and selects a time null basis from the PCA bases (step SC4).

In parallel with step SC1 to SC4, the processing circuitry 11 performs view-sharing reconstruction based on time-series sparse sampling+ACS line k-space data to generate an image (hereinafter referred to as a view-sharing image) through implementation of the image conversion function 112 (step SC5). Specifically, in step SC5, the processing circuitry 11 performs, based on the time-series sparse sampling+ACS line k-space data, view sharing on any single frame of the sparse sampling+ACS line k-space data to interpolate k-space data of a missing k-space line of the frame of the sparse sampling+ACS line k-space data. The processing circuitry 11 then performs an image conversion on the k-space data after view sharing to generate a converted image (hereinafter referred to as a view-sharing image).

After step SC5, the processing circuitry 11 performs a principal component analysis with respect to the image space axis direction on the view-sharing image to calculate a plurality of PCA bases, as in steps SB2 to SB3 of the second example (step SC6), and selects an image space null basis from the PCA bases (step SC7). The principal component analysis with respect to the image space axis direction may be performed by a method similar to that of step SB2 of the second example.

After steps SC4 and SC7, the processing circuitry 11 generates time-series output images based on the time-series sparse sampling+ACS line k-space data, the time null basis selected in step SC4, and the image space null basis selected in step SC7, through implementation of the basis utilization function 115 (step SC8). Specifically, the processing circuitry 11 minimizes the error function EI(x) exemplified in the following equation (4) under a constraint condition wherein the constraint term is equal to zero or not more than a predetermined value.

$$EI(x) = \|FSx - y\|_2^2 + \lambda 1\|R1x\|_2^2 + \lambda 2\|R2x\|_2^2 \qquad (4)$$

As shown in equation (4), the constraint term according to the third example is defined by, for example, the sum of a constraint term $\lambda 1\|R1x\|_2^2$ relating to the time null basis and a constraint term $\lambda 2\|R2x\|_2^2$ relating to the image space null basis. R1 is a matrix notation of the time null basis, $\lambda 1$ is an eigenvalue of the time null basis R1, R2 is a matrix notation of the image space null basis, and $\lambda 2$ is an eigenvalue of the image space null basis R2. The processing circuitry 11 determines an updated image x that satisfies all of the constraint conditions of the constraint terms $\lambda 1\lambda R1x\|_2^2$ and $\lambda 2\|R2x\|_2^2$ and the minimization condition of the error function EI(x) while sequentially changing the pixel value of each pixel of the updated image x. The processing circuitry 11 may alternately make a determination on the constraint condition relating to $\lambda 1\|R1x\|_2^2$ and the constraint condition relating to $\lambda 2\|R2x\|_2^2$, or may repeatedly make a determination on the constraint conditions relating to $\lambda 1\|R1x\|_2^2$ and $\lambda 2\|R2x\|_2^2$. Also in equation (4), instead of $\lambda 1$ and $\lambda 2$, a diagonal weighting matrix W1 and a diagonal weighting matrix W2 may be used respectively, as shown in equation (2).

After step SC8, the processing circuitry 11 performs noise reduction processing on the time-series output images generated in step SC8, through implementation of the image processing function 116 (step SC9). The noise reduction processing in step SC9 may be performed in a manner similar to that in step SA6.

After step SC9, the processing circuitry 11 determines whether or not to terminate the null-space-constraint reconstruction (step SC10). In step SC10, the processing circuitry 11 determines whether or not a termination condition is met. The termination condition may be, for example, that the number of repetitions has reached a predetermined number, that the image quality evaluation index of the SNR of the reduced-noise image is smaller than or equal to a threshold, or any other condition. The processing circuitry 11 determines not to terminate the null-space-constraint reconstruction when the termination condition is not met, and determines to terminate the null-space-constraint reconstruction when the termination condition is met.

When it is determined to not terminate the null-space-constraint reconstruction (No in SC10), the processing circuitry 11 performs a data conversion on the time-series noise-reduced images generated in step SC9 to generate time-series computational k-space data, through implementation of the data conversion function 117 (step SC11). After step SC11, the processing circuitry 11 generates new time-series output images based on the time-series computational k-space data generated in step SC11, the time null basis selected in step SC4, and the image space null basis selected in step SC7 (step SC8), and executes noise reduction processing on the new time-series output images generated in step SC8 (step SC9). Then, the processing circuitry 11 determines again whether or not to terminate the null-space-constraint reconstruction (step SC10). In this manner, the processing circuitry 11 repeats steps SC8 to SC11 until it is determined that the termination condition is met in step SC10.

When it is determined to terminate the null-space-constraint reconstruction (Yes in SC10), the processing circuitry 11 causes the display 13 to display the time-series reduced-noise images generated in step SC9, stores the time-series reduced-noise images in the memory device 15, or transmits the time-series reduced-noise images to another computer via the communication interface 12, through implementation of the output control function 118.

The processing including null-space-constraint reconstruction according to the third example is thereby completed.

The above-described processing including null-space-constraint reconstruction according to the third example is a mere example, and may be modified in various ways. For example, a principal component analysis with respect to the temporal axis direction is described above as being performed on center images; however, the principal component analysis with respect to the temporal axis direction may be performed on any converted images such as converted images based on sparse sampling+ACS line k-space data. Also, a principal component analysis with respect to the image space axis direction is described as being performed on a view-sharing image; however, the principal component analysis with respect to the image space axis direction may be performed on any converted image as in the second example.

As described above, the processing circuitry 11 according to the third example calculates a plurality of bases by performing a basis conversion with respect to the temporal axis direction on time-series images based on time-series k-space data, and selects a time null basis with a relatively low contribution rate from among the calculated bases. The processing circuitry 11 also calculates a plurality of bases by performing a basis conversion with respect to the image space axis direction on a single image, and selects an image space null basis with a relatively low contribution rate from among the calculated bases. The processing circuitry 11 then generates time-series output images by performing null-space-constraint construction on time-series k-space data using a null space spanned by the time null basis and a null space spanned by the image space null basis as constraint conditions.

The above configuration enables reconstruction using both information on the temporal axis direction and information on the image space axis direction. Thus, image quality is expected to improve in comparison with the first example and the second example.

Fourth Example

A fourth example is a modification of the third example. The processing circuitry 11 according to the fourth example obtains an image space null basis by utilizing k-space data (hereinafter referred to as T1-weighted k-space data) acquired by T1-weighted data acquisition in null-space-constraint reconstruction on time-series k-space data (hereinafter referred to as T2-weighted k-space data) acquired by T2-weighted data acquisition.

Figure 10:
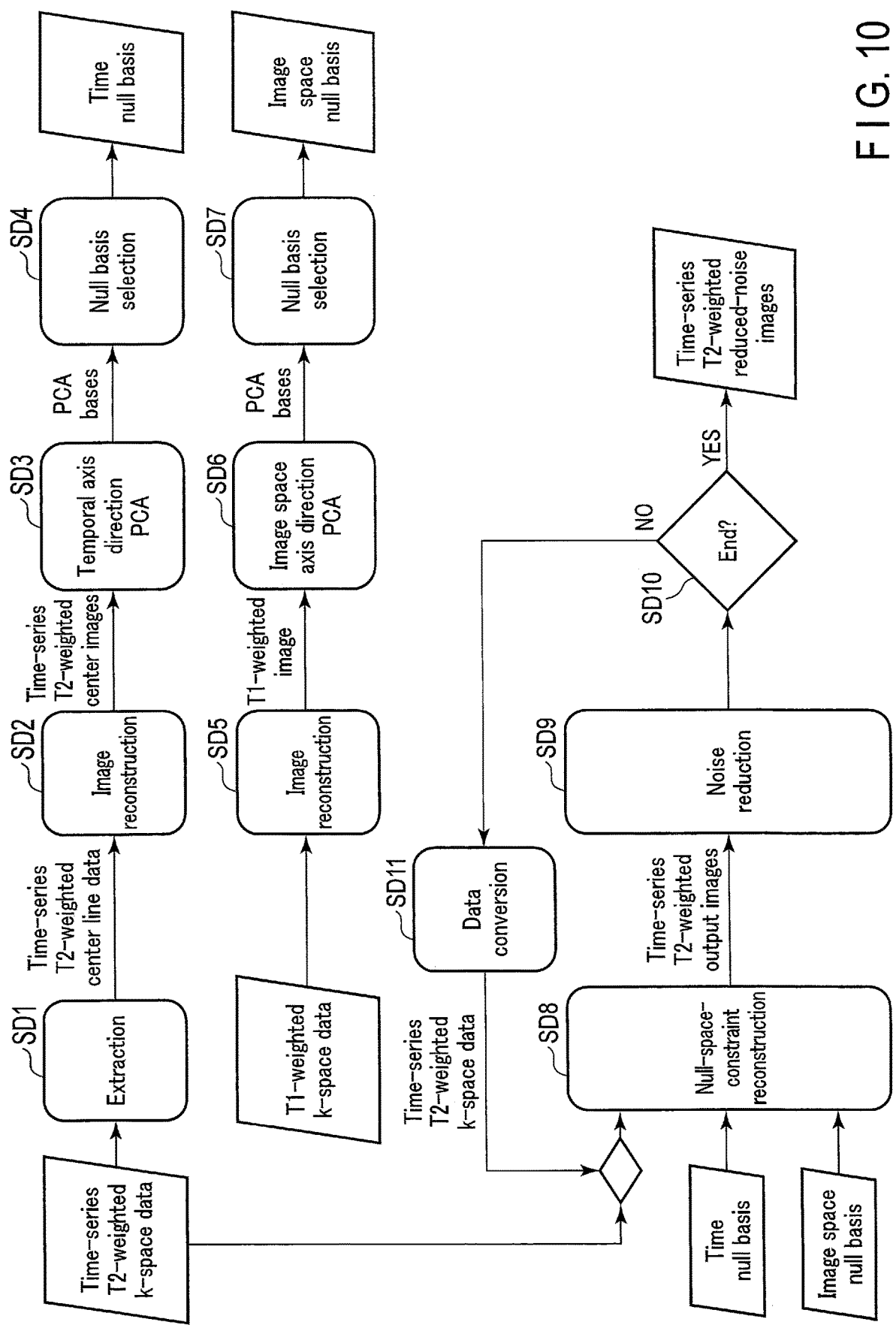
FIG. 10 schematically shows a processing example including null-space-constraint reconstruction by the information processing apparatus according to a fourth example.

FIG. 10 schematically shows a processing example including null-space-constraint reconstruction by the information processing apparatus 1 according to the fourth example. As shown in FIG. 10, the processing circuitry 11 first obtains time-series T2-weighted k-space data as well as T1-weighted k-space data through implementation of the obtainment function 111. The T2-weighted k-space data is acquired by a magnetic resonance imaging apparatus executing T2-weighted data acquisition on a subject. The T1-weighted k-space data is acquired by a magnetic resonance imaging apparatus executing T1-weighted data acquisition on the same subject. The order in which T2-weighted data acquisition and T1-weighted data acquisition are performed is not particularly limited, and T2-weighted data acquisition may be performed before or after T1-weighted data acquisition.

In the fourth example, T2-weighted data acquisition is used for the principal component analysis with respect to the temporal axis direction; therefore, T2-weighted data acquisition requires video imaging, and is preferably executed at a higher acceleration rate than T1-weighted data acquisition. In the fourth example, T1-weighted data acquisition is used for the principal component analysis with respect to the image space axis direction; therefore, T1-weighted data acquisition requires high sampling rate acquisition, and is preferably executed at a lower acceleration rate than T2-weighted data acquisition. For example, T2-weighted data acquisition may be sparse sampling acquisition at the sextuple acceleration rate, and T1-weighted data acquisition may be sparse sampling acquisition at the double acceleration rate. These acceleration rates are mere examples, and are not limited to the above-described rates. T1-weighted data acquisition may be performed at the one-fold acceleration rate, i.e., may be full sampling acquisition. T1-weighted k-space data may be one frame of time-series T1-weighted data, or may be one frame of k-space data based on time-series T1-weighted data, such as average data of time-series T1-weighted data.

As shown in FIG. 10, the processing circuitry 11 extracts time-series T2-weighted center line data from time-series T2-weighted k-space data as in the first example (step SD1), performs image reconstruction on the time-series T2-weighted center line data to generate time-series T2-weighted center images (step SD2), performs a principal component analysis with respect to the temporal axis on the time-series T2-weighted center images to calculate a plurality of PCA bases (step SD3), and selects a time null basis from the PCA bases (step SD4).

In parallel with steps SD1 to SD4, the processing circuitry 11 performs image reconstruction on T1-weighted k-space data to generate a T1-weighted image through implementation of the image conversion function 112 (step SD5). In step SD5, the processing circuitry 11 may perform parallel imaging (PI) reconstruction on T1-weighted k-space data to generate a T2-weighted image in order to reduce wrap-around artifacts caused by sparse sampling acquisition. Instead of PI reconstruction, the processing circuitry 11 may fill zeros into the missing k-space lines of T1-weighted k-space data, and generate a T1-weighted image by image reconstruction based on the k-space data after zero filling. As another method, when time-series T1-weighted k-space data has been acquired, the processing circuitry 11 may perform view-sharing reconstruction on the time-series T1-weighted k-space data to generate a T1-weighted image.

After step SD5, the processing circuitry 11 performs a principal component analysis with respect to the image space axis direction on the T1-weighted image to calculate a plurality of PCA bases, as in steps SB2 and SB3 of the second example (step SD6), and selects an image space null basis from the PCA bases (step SD7). The principal component analysis with respect to the image space axis direction may be performed with a method similar to that of step SB2 of the second example.

After steps SD4 and SC7, the processing circuitry 11 generates time-series T2-weighted output images based on the time-series T2-weighted k-space data, the time null basis selected in step SD4, and the image space null basis selected in step SD7, through implementation of the basis utilization function 115 (step SD8). The null-space-constraint reconstruction in step SD8 can be performed in a method similar to that of the null-space-constraint reconstruction of the third example.

After step SD8, the processing circuitry 11 performs noise reduction processing on the time-series output images generated in step SD8 to generate time-series T2-weighted reduced-noise images, through implementation of the image processing function 116 (step SD9). The noise reduction processing in step SD9 may be performed in a manner similar to that in step SA6.

After step SD9, the processing circuitry 11 determines whether or not to terminate the null-space-constraint reconstruction (step SD10). In step SD10, the processing circuitry 11 determines whether or not a termination condition is met. The termination condition may be, for example, that the number of repetitions has reached a predetermined number, that the image quality evaluation index of the SNR of each T2-weighted reduced-noise image is smaller than or equal to a threshold, or any other condition. The processing circuitry 11 determines not to terminate the null-space-constraint reconstruction when the termination condition is not met, and determines to terminate the null-space-constraint reconstruction when the termination condition is met.

When it is determined to not terminate the null-space-constraint reconstruction (No in SD10), the processing circuitry 11 performs a data conversion on the time-series T2-weighted noise-reduced images generated in step SD9 to generate time-series T2-weighted computational k-space data, through implementation of the data conversion function 117 (step SD11). After step SD11, the processing circuitry 11 generates new time-series T2-weighted output images based on the time-series T2-weighted computational k-space data generated in step SD11, the time null basis selected in step SD4, and the image space null basis selected in step SD7 (step SD8), and executes noise reduction processing on the new time-series T2-weighted output images generated in step SD8 (step SD9). Then, the processing circuitry 11 determines again whether or not to terminate the null-space-constraint reconstruction (step SD10). In this manner, the processing circuitry 11 repeats steps SD8 to SD11 until it is determined that the termination condition is met in step SD10.

When it is determined to terminate the null-space-constraint reconstruction (Yes in SD10), the processing circuitry 11 causes the display 13 to display the time-series T2-weighted reduced-noise images generated in step SD9, stores the time-series T2-weighted reduced-noise images in the memory device 15, or transmits the time-series T2-weighted reduced-noise images to another computer via the communication interface 12, through implementation of the output control function 118.

The processing including null-space-constraint reconstruction according to the fourth example is thereby completed.

The above-described processing including null-space-constraint reconstruction according to the fourth example is a mere example, and may be modified in various ways. For example, T1-weighted k-space data and T2-weighted k-space data are described as being used in the above example; however, the present example is not limited to this, and k-space data acquired by any data acquisition method may be used. For example, T1-weighted k-space data and/or T2-weighted k-space data may be replaced with k-space data acquired by any data acquisition, such as proton density-weighted k-space data acquired by proton density-weighted data acquisition or diffusion-weighted k-space data acquired by diffusion-weighted image acquisition.

As described above, the processing circuitry 11 according to the fourth example calculates a plurality of bases by performing a basis conversion with respect to the temporal axis direction on time-series images based on time-series k-space data acquired by a first data acquisition method, and selects a time null basis with a relatively low contribution rate from among the calculated bases. The processing circuitry 11 also calculates a plurality of bases by performing a basis conversion with respect to the image space axis direction on a single image acquired by a second data acquisition method, and selects an image space null basis with a relatively low contribution rate from among the calculated bases. The processing circuitry 11 then generates time-series output images by performing, on the time-series k-space data acquired by the first data acquisition method, null-space-constraint reconstruction using a null space spanned by the time null basis and a null space spanned by the image space null basis as constraint conditions.

The above configuration makes it possible to obtain a time null basis using an image based on a data acquisition method by which a temporal correlation can be easily obtained, and obtain an image space null basis using an image based on a data acquisition method by which an image space correlation can be easily obtained; therefore, image quality of the output image is expected to be improved.

Fifth Example

The processing circuitry 11 according to a fifth example performs, through the basis conversion function 113, a basis conversion with respect to a scan parameter value axis on image data. The basis conversion with respect to a scan parameter value axis is a basis conversion performed on image data aligned along a scan parameter value axis. The scan parameter value axis refers to a coordinate axis relating to a scan parameter value. As the scan parameter, for example, a b-value, which is an application intensity of a motion probing gradient (MPG) in diffusion-weighted image acquisition, is used.

Figure 11:
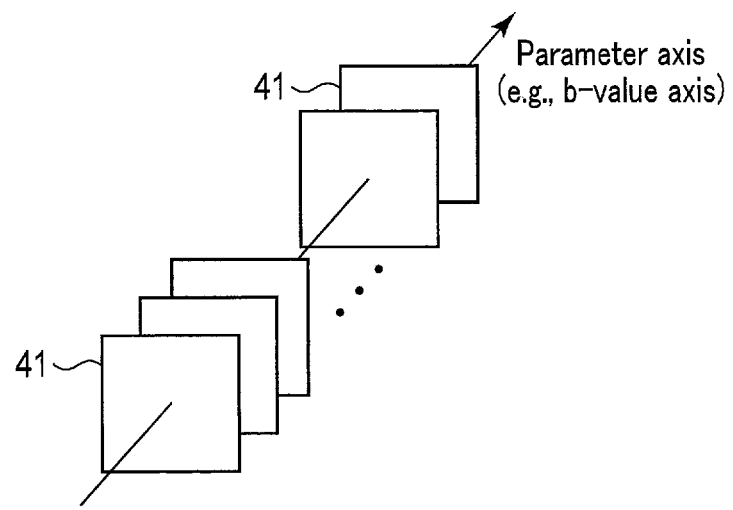
FIG. 11 schematically shows a basis conversion with respect to a parameter axis direction according to a fifth example.

FIG. 11 schematically shows a basis conversion with respect to the parameter axis direction according to the fifth example. As shown in FIG. 11, the processing circuitry 11 first generates a plurality of diffusion-weighted images 41 based on a plurality of k-space data items relating to a plurality of b-values. The k-space data items relating to b-values are acquired by a magnetic resonance imaging apparatus executing diffusion-weighted image acquisition while sequentially changing the b-value, which is a scan parameter. The diffusion-weighted images 41 are arranged along the b-value axis in a three-dimensional space (hereinafter referred to as an xy-b space) defined by two dimensions of image axes and one dimension of a b-value axis. The b-value axis is a coordinate axis defining the b-values of diffusion-weighted image acquisitions for acquiring k-space data items corresponding to the diffusion-weighted images 41. The diffusion-weighted images 41 are highly correlated with respect to the b-value axis direction.

The processing circuitry 11 performs a principal component analysis on a plurality of diffusion-weighted images 41 arranged in the xy-b space. Specifically, the processing circuitry 11 records the change in the pixel value along the b-value axis for all pixels of the diffusion-weighted images 41. For example, for each pixel, a vector indicating the change in the pixel value along the b-value axis can be obtained. The number of elements of the vector corresponds to the number of diffusion-weighted images. The processing circuitry 11 then performs a principal component analysis on a plurality of pixel value change vectors relating to a plurality of pixels to calculate the same number of PCA bases as the b-values (the same number as the diffusion-weighted images 41), and selects a null basis (hereinafter referred to as a b-value null basis) from the PCA bases. Then, the processing circuitry 11 can generate an output image by performing an image conversion on the k-space data items relating to the b-values using the null space spanned by the b-value null basis as a constraint condition.

The scan parameter relating to the fifth example is not limited to the b-value, and may be any scan parameter such as an echo time (TE) or a repetition time (TR).

As described above, the processing circuitry 11 according to the fifth example calculates a plurality of bases by performing a basis conversion with respect to the scan parameter axis direction on a plurality of images based on a plurality of k-space data items relating to a plurality of scan parameter values, selects a null basis with a relatively low contribution rate from among the calculated bases, and generates a plurality of output images by performing, on the k-space data items, null-space-constraint reconstruction using a null space spanned by the null basis as a constraint condition.

According to the above configuration, a null space spanned by a null basis derived from a basis conversion with respect to the scan parameter axis direction is used as a constraint condition; therefore, in the reconstruction process, information with a low scan-parameter-value-related correlation included in scan parameter series images is actively lightened, whereas information with a high scan-parameter-value-related correlation is passively weighted, relatively. Accordingly, the fifth example enables reconstruction using information in the scan parameter value axis direction.

Sixth Example

The processing circuitry 11 according to a sixth example performs, through the basis conversion function 113, a basis conversion with respect to a contrast axis direction on image data. The basis conversion with respect to a contrast axis direction is a basis conversion performed on image data aligned along a contrast axis. The contrast axis refers to a coordinate axis relating to a contrast type. Examples of the contrast type include T1 weighting, T2 weighting, and proton density weighting.

Figure 12:
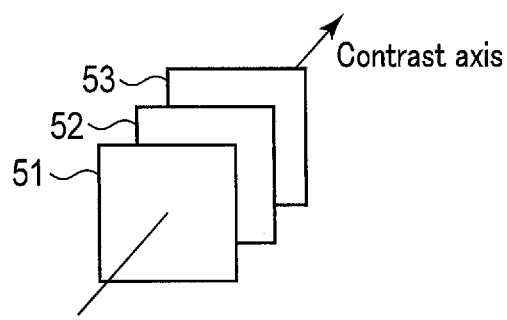
FIG. 12 schematically shows a basis conversion with respect to a contrast axis direction according to a sixth example.

FIG. 12 schematically shows a basis conversion with respect to the contrast axis direction according to the sixth example. As shown in FIG. 12, a plurality of MR images of different contrast types are obtained. For example, a T1-weighted image 51 corresponding to T1 weighting, a T2-weighted image 52 corresponding to T2 weighting, and a proton density-weighted image 53 corresponding to proton density weighting are obtained. The T1-weighted image 51, T2-weighted image 52, and proton density-weighted image 53 are acquired by a magnetic resonance imaging apparatus performing data acquisition while sequentially changing the TR and TE. The T1-weighted image 51, T2-weighted image 52, and proton density-weighted image 53 are arranged along the contrast axis in a three-dimensional space (hereinafter referred to as an xy-c space) defined by two dimensions of image axes and one dimension of a contrast axis. The T1-weighted image 51, T2-weighted image 52, and proton density-weighted image 53 are highly correlated with respect to the contrast axis.

The processing circuitry 11 performs a principal component analysis on the T1-weighted image 51, T2-weighted image 52, and proton density-weighted image 53 arranged in the xy-c space. Specifically, the processing circuitry 11 records the change in the pixel value along the contrast axis for all pixels of the T1-weighted image 51, T2-weighted image 52, and proton density-weighted image 53. For example, for each pixel, a vector indicating the change in the pixel value along the contrast axis can be obtained. The number of elements of the vector corresponds to the number of images arranged in the xy-c space. The processing circuitry 11 then performs a principal component analysis on a plurality of pixel value change vectors relating to a plurality of pixels to calculate the number of PCA bases corresponding to the number of contrast types (the number of images arranged in the xy-c space), and selects a null basis (hereinafter referred to as a contrast null basis) from the PCA bases. Then, the processing circuitry 11 can generate an output image by performing an image conversion on k-space data items relating to the contrast types using the null space spanned by the contrast null basis as a constraint condition.

The contrast types according to the sixth example are not limited to T1 weighting, T2 weighting, and proton density weighting, and may be any contrast types such as T1 weighting, T2 weighting, and center frequency (f0) weighting. In the above example, a single image is described as being used for each contrast type; however, two or more images may be used for each contrast type. As the two or more images of the same contrast type, images of different scan parameter values such as b-values, TEs, and TRs may be used.

As described above, the processing circuitry 11 according to the sixth example calculates a plurality of bases by performing a basis conversion with respect to the contrast axis direction on a plurality of images based on a plurality of k-space data items relating to a plurality of contrast types, selects a null basis with a relatively low contribution rate from among the calculated bases, and generates a plurality of output images by performing, on the k-space data items, null-space-constraint reconstruction using a null space spanned by the contrast null basis as a constraint condition.

According the above configuration, a null space spanned by a contrast null basis obtained by a basis conversion with respect to the contrast axis direction is used as a constraint condition; therefore, in the reconstruction process, information with a low contrast-related correlation included in contrast series images is actively lightened, whereas information with a high contrast-related correlation is passively weighted relatively. Accordingly, the sixth example enables reconstruction using information in the contrast axis direction.

Seventh Example

In some examples described above, null-space-constraint reconstruction using a null basis is described as being applied to k-space data corresponding to an image used for calculation of the null basis. However, the present embodiment is not limited to this, and null-space-constraint reconstruction using a null basis may be applied to k-space data other than the k-space data corresponding to an image used for calculation of the null basis. For example, when N data acquisitions (where N is any integer) are performed on the same subject, it is possible to calculate a null basis from a converted image based on k-space data acquired by the p-th data acquisition ($1 \leq p \leq N$), and apply null-space-constraint reconstruction using the null basis on k-space data acquired by the q-th data acquisition ($1 \leq q \leq N$, $q \neq p$). The temporal order of p and q is not particularly limited, and p may be temporally before or after q. The p-th data acquisition and the q-th data acquisition need not be performed in the same inspection and, for example, the p-th data acquisition may be an acquisition performed in a past inspection conducted several days, several weeks, several month, or several years earlier than the inspection of the q-th data acquisition.

When the p-th data acquisition and the q-th data acquisition are performed by the same data acquisition method, the accuracy of null-space-constraint reconstruction on the q-th data acquisition can be more reliably guaranteed than when they are performed by different data acquisition methods. However, the p-th data acquisition and the q-th data acquisition may be performed by different data acquisition methods. Namely, a null basis obtained for an image based on k-space data by a first data acquisition method may also be used for null-space-constraint reconstruction for k-space data by a second data acquisition method. When the p-th data acquisition and the q-th data acquisition are performed on the same subject, the accuracy of null-space-constraint reconstruction on the q-th data acquisition can be more reliably guaranteed than when they are performed on different subjects. However, the p-th data acquisition and the q-th data acquisition may be performed on different subjects. Namely, the null basis obtained in connection with a first subject may also be used for a second subject.

Eighth Example

Null-space-constraint reconstruction in at least one example described above may be implemented by a neural network such as a CNN. In this case, the error function in equation (1), (2), (3), or (4) may be incorporated in a neural network such as a CNN by, for example, model-based reconstruction using deep learned priors (MoDL). In this case, null-space-constraint reconstruction and post processing such as noise reduction processing may be incorporated into the neural network.

Comparative examples of the space constraint reconstruction according to the present embodiment include self-calibration type low rank model reconstruction using a primary space spanned by a principle basis. This self-calibration type low rank model reconstruction requires time for construction of the low rank model. This is prominent in construction of a low rank model using singular value decomposition. In addition, it is considered to be difficult to incorporate the self-calibration type low rank model reconstruction into a neural network such as a CNN. This is because it is necessary to first project image data to a low rank model and evaluate an error between the projection amount and the previous projection amount. A pre-trained type low rank model has fewer processing time weak points; however, since the used basis is not a basis based on image data to be reconstructed, the dimension reduction effect is reduced. Accordingly, the self-calibration type low rank model reconstruction is difficult to use in practice.

In contrast, the null-space-constraint reconstruction according to the present embodiment is easier to use in practice than the self-calibration type low rank model reconstruction according to the comparative example. For example, as shown in equation (1), the null-space-constraint reconstruction does not require evaluation of an error in the projection amount to the null space, and can be easily incorporated into a neural network. In addition, since the projection amount of image data to a null basis, which is not a principle basis, is zero or noise, the load of calculation of the projection amount, etc. can be small.

Ninth Example

According to some examples described above, the error function EI(x) or error function ED(x) includes a data consistency term, as shown in equations (1) to (4). However, the present embodiment is not limited to this. Even when the data consistency term is unknown, the image x may be updated by regarding, for example, the following equation (5) as a constraint equation (constraint term). Equation (5) corresponds to equation (1) and corresponds to an example in which the null space R is applied in the image space.

$$EI(x) = \lambda \|Rx\|_2^2 \qquad (5)$$

The above-described null-space-constraint reconstruction is a method premised on the presence of a data consistency term; however, for example, projection onto convex sets (POCS) may be utilized to satisfy each constraint equation regardless of the presence/absence of a data consistency term. For example, when it is desired for the constraint equation to be applied to a feature amount sequence instead of time-series images, a data consistency term cannot be obtained; however, POCS can be utilized even in such a case. POCS can also be applied to time-series images.

For example, when time-series k-space data is used as raw data, the processing circuitry 11 according to a ninth example first performs an image conversion on time-series k-space data to generate time-series images, through implementation of the image conversion function 112. Then, the processing circuitry 11 generates an output image by solving the minimization problem of the constraint equation, such as the above equation (5), defined by a norm of the projection amounts of the time-series images by POCS to a null space, through implementation of the basis utilization function 115.

When POCS is utilized, projection Rx of a feature amount sequence x to a null space R is achieved by POCS. The projection amount of a feature amount sequence to a null space belongs to a convex set. The constraint equation of equation (5) includes composition of I constraint equations as a projection operation of projection to a null space using POCS. The number I corresponds to the number of time-series images to be projected, i.e., the number of repetitions of a sequential operation in the null-space-constraint reconstruction using equation (1), etc. The i-th constraint equation (1≤i≤I) represents projection of the i-th feature amount series (1≤i≤I) to the null space.

Where the projection amount to the null space R which is necessary to satisfy the i-th constraint equation without an error is represented by POCS(i), the projection amount to the null space R is max(0,POCS(i)−POCS_threshold) (where the constant POCS_threshold, which is separately determined, satisfies POCS_threshold≥0) or POCS(i)□POCS_weight (where the constant POCS_weight, which is separately determined, satisfies 0≤POCS_weight<1). POCS(i)−POCS_threshold means that the projection amount to the null space R is uniformly decreased by POCS_threshold, and when POCS(i)−POCS_threshold is negative, the i-th projection operation is stopped based on a max operation of the negative value and 0. POCS(i)□POCS_weight means multiplying of the projection amount to the null space R by POCS_weight so as to multiply the projection amount by a constant. In this way, the influence of the constraint equation can be controlled by adjusting POCS_threshold or POCS_weight.

As in equation (2), even when the error function does not include a data consistency term, the eigenvalue λ can be replaced with the weighting matrix W, as shown in equation (6).

$$EI(x) = \|WRx\|_2^2 \qquad (6)$$

For example, each matrix element of the weighting matrix W may be set to, for example, a value obtained by multiplying the eigenvalue λ by POCS_threshold or a value obtained by multiplying the reciprocal of the square root of the eigenvalue λ by POCS_weight.

These constraint equations can be implemented, for example, by a neural network in which a projection operation of POCS is incorporated as a linear operation without a constant to be trained. For example, they may be implemented by a neural network in which a neural network (hereinafter referred to as an "NN layer") that performs arbitrary processing and a neural network layer (hereinafter referred to as a "POCS layer") that performs a POCS operation are alternately inserted.

Figure 13:
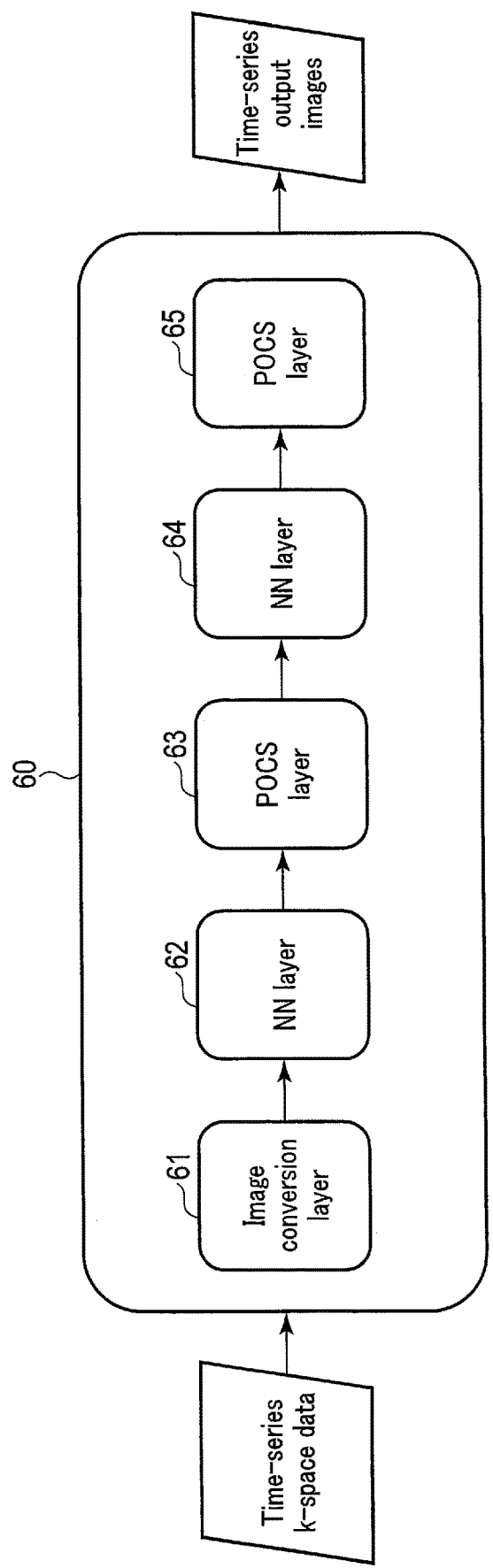
FIG. 13 shows a configuration example of an integrated neural network according to a ninth example.

FIG. 13 shows a configuration example of an integrated neural network 60 according to the ninth example. As shown in FIG. 13, the integrated neural network 60 is a deep neural network including an image conversion layer 61, an NN layer 62, a POCS layer 63, an NN layer 64, and a POCS layer 65. The image conversion layer 61 converts time-series k-space data into a feature amount sequence. The NN layers 62 and 64 each perform given processing on a feature amount sequence. The NN layers 62 and 64 may calculate adjustment values, such as POCS_threshold or POCS_weight, to be used by the subsequent POCS layers 63 and 65. The POCS layers 63 and 65 each perform null-space-constraint reconstruction by a POCS operation according to the constraint equation of equation (5) or (6) and generate time-series output images from a feature amount sequence.

The integrated neural network 60 can be generated by training of a pre-training type or an end-to-end type. Training of the pre-training type can be performed in accordance with, for example, the following procedure. First, the processing circuitry 11 separately trains the NN layer 62, the POCS layer 63, the NN layer 64, and the POCS layer 65. Next, the processing circuitry 11 connects the NN layer 62, the POCS layer 63, the NN layer 64, and the POCS layer 65 as shown in FIG. 13, and trains them as one deep neural network. In this manner, the integrated neural network 60 can be generated. In the case of the end-to-end type, the processing circuitry 11 may train one deep neural network to output time-series output images in response to an input of time-series k-space data.

Directly connecting a unit layer including the NN layer 62 and the POCS layer 63 to a unit layer including the NN layer 64 and the POCS layer 65 can improve image quality of the time-series images. The number of unit layers directly connected to each other is not limited to two, and may be three or more. The integrated neural network 60 may include any layer other than the image conversion layer, the NN layers, and the POCS layers.

Tenth Example

Signal data according to a tenth example is MRS (MR spectroscopy) spectrum data acquired by a magnetic resonance imaging apparatus. The MRS spectrum data is waveform data of an MRS spectrum representing a frequency series corresponding to signal strength values. More specifically, the MRS spectrum represents a signal strength value of each chemical shift frequency. The signal strength value depends on the contained amounts of substances, such as a molecule and metabolite, having corresponding chemical shift frequencies. The data processing by the basis utilization function 115 according to the tenth example is assumed to be noise reduction.

The processing circuitry 11 first obtains MRS spectrum data acquired by a resonance imaging apparatus, through implementation of the obtainment function ill. The MRS spectrum data includes a plurality of MRS spectra relating to a plurality of positions. The processing circuitry 11 then performs a basis conversion with respect to the frequency axis direction on the MRS spectrum data, through implementation of the basis conversion function 113. Namely, the processing circuitry 11 performs a basis conversion on a plurality of MRS spectra included in MRS spectrum data to calculate a plurality of bases. The processing circuitry 11 selects a specific basis (null basis) from among the bases, through implementation of the selection function 114. Then, the processing circuitry 11 generates a plurality of noise-reduced MRS spectra by performing, on the MRS spectra, noise reduction processing using a null space spanned by the null basis as a constraint condition, through implementation of the basis utilization function 115.

As an example, an MRS spectrum is acquired at 25 points in an xy space, each represented by two dimensions, x and y, and each MRS spectrum includes signal strength values of 10 molecules. In this case, the 25 MRS spectra are arranged along the frequency axis in a three-dimensional space (hereinafter referred to as an xy-f space) defined by two dimensions of space axes and one dimension of a frequency axis. A principal component analysis is performed on the 25 MRS spectra arranged in the xy-f space, and 25 PCA bases are calculated. From the 25 PCA bases, about five principle bases are rejected, and the remaining PCA bases are selected as null bases.

The noise reduction processing may be achieved by equation (1), (2), (3) or (4), or by minimizing the error function EI(x) shown in the above equation (5) or (6) utilizing, for example, POCS. In the case of the tenth example, x represents MRS spectrum data on which given noise reduction processing has been performed. R represents the above-described selected null bases. Specifically, in the noise reduction processing, the processing circuitry 11 first performs given noise reduction processing using a smoothing filter or the like on MRS spectrum data. The processing circuitry 11 then applies the noise-reduced MRS spectrum data to the null space R to calculate a projection amount Rx, and calculates the error function EI(x) shown in equation (5) or (6) based on the projection amount Rx. The processing circuitry 11 repeats the noise reduction processing and calculation of the error function to determine MRS spectrum data x that minimizes the error function EI(x). The noise reduction processing is thereby completed.

Figure 14:
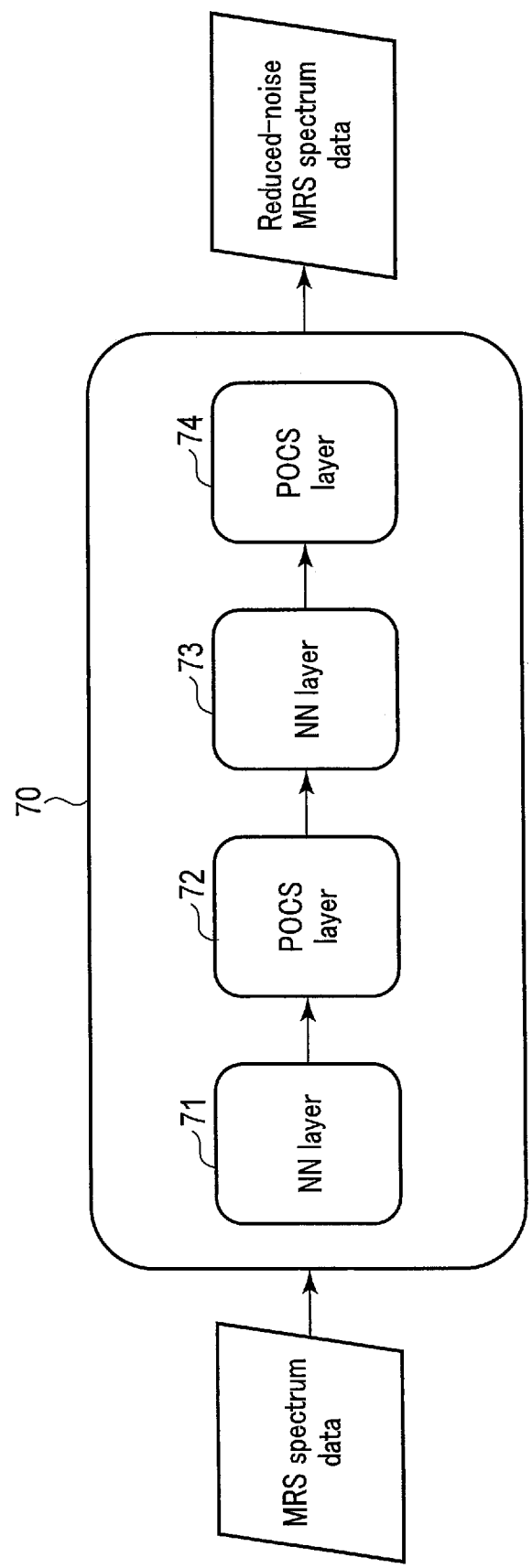
FIG. 14 shows a configuration example of an integrated neural network according to a tenth example.

FIG. 14 shows a configuration example of an integrated neural network 70 according to the tenth example. As shown in FIG. 14, the integrated neural network 70 is a deep neural network including an NN layer 71, a POCS layer 72, an NN layer 73, and a POCS layer 74. The NN layer 71 and NN layer 73 execute noise reduction processing on MRS spectrum data. The NN layers 62 and 64 may calculate adjustment values, such as POCS_threshold or POCS_weight, to be used by the subsequent POCS layers 63 and 65. The POCS layers 72 and 74 perform a POCS operation according to a constraint equation such as equation (5) or (6) on the MRS spectrum data output from the NN layers 71 and 73. Final noise-reduced MRS spectrum data is output from the POCS layer 74. The number of NN layers 71, 73 and the number of POCS layers 72, 74 are not limited to two, and may be any number not less than one. An NN layer may be connected to the POCS layer 74, and the output of the NN layer may be used as the final noise-reduced MRS spectrum data.

Eleventh Example

Data processing by the basis utilization function 115 according to the eleventh example is segmentation processing (or partial area classification processing) in which, for example, whether or not each pixel (or partial area) of image data belongs to a specific area is converted into a number and output. Segmentation processing using a null space as a constraint condition will be referred to as null-space-constraint segmentation.

Figure 15:
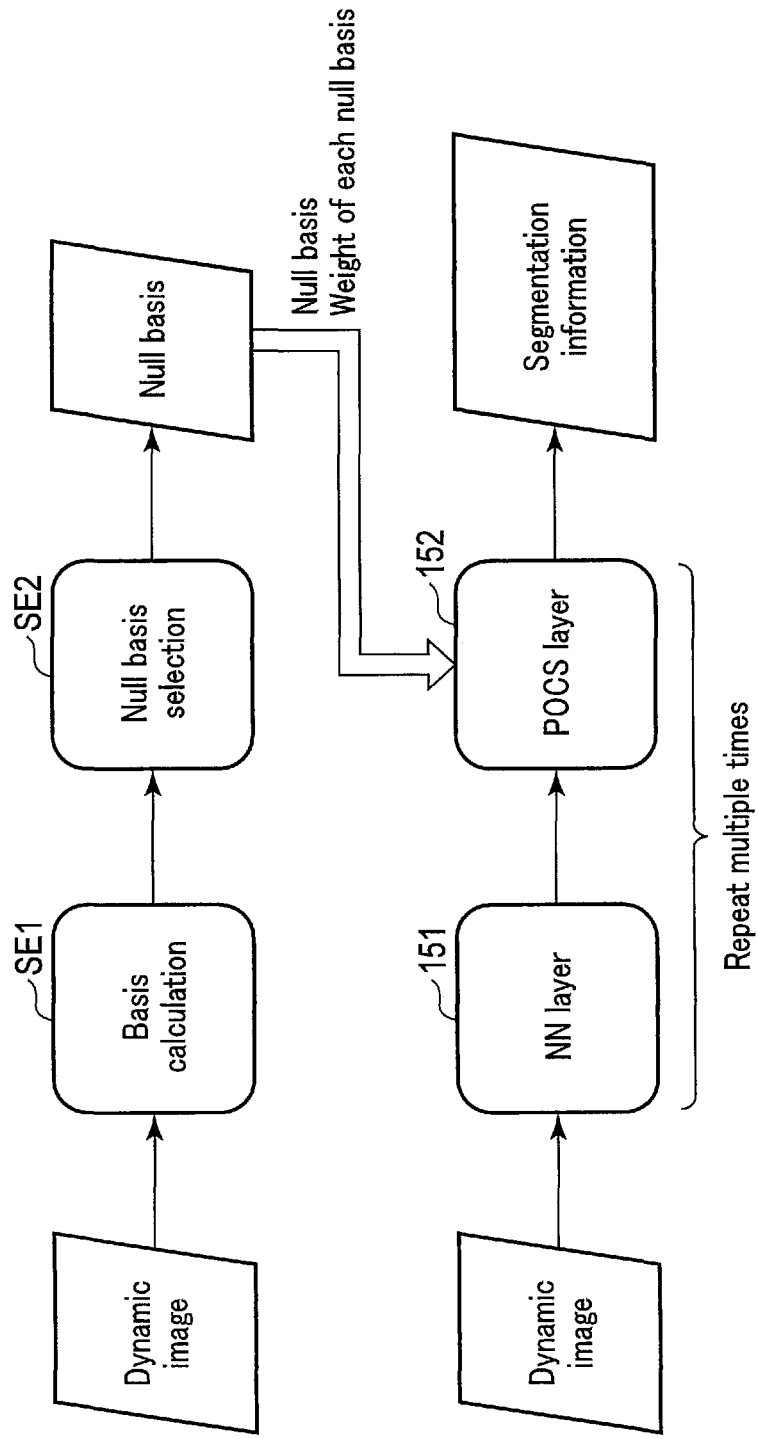
FIG. 15 shoes a flow of a series of processes relating to null-space-constraint segmentation by the information processing apparatus according to an eleventh example.

FIG. 15 shows a flow of a series of processes relating to null-space-constraint segmentation by the information processing apparatus according to the eleventh example. As shown in FIG. 15, the processing circuitry 11 obtains image data of a video image, and calculates a plurality of PCA bases by performing on the video image a basis conversion with respect to the temporal axis direction, through implementation of the basis conversion function 113 (step SE1). Then, the processing circuitry 11 selects null bases from the PCA bases through implementation of the selection function 114 (step SE2).

As shown in FIG. 15, the processing circuitry 11 calculates an intermediate output value by inputting the image data of the video image to an NN layer 151, and calculates segmentation information by inputting the intermediate output value to a POCS layer 152, through implementation of the basis utilization function 115. The NN layer 151 calculates segmentation information from a video image. The POCS layer 152 performs a POCS operation according to a constraint equation, such as equation (5) or (6), on the segmentation information from the NN layer 151 based on the null bases obtained in step SE2 and a weight of each null basis. Final segmentation information is output from the POCS layer 152. The parameter of the NN layer 151 is trained so that the NN layer 151 outputs segmentation information in response to an input of a video image. The NN layer 151 and POCS layer 152 may be repeated multiple times.

The POCS layer 152 may apply the POCS operation to an intermediate output value of the segmentation processing. Alternatively, the processing circuitry 11 may calculate a null basis from an ECG signal acquired in parallel with an image, and execute data processing on the image using the null basis based on the ECG signal. Alternatively, the processing circuitry 11 may calculate a null basis from a water signal acquired in MRS, and execute data processing on metabolism using the null basis.

Twelfth Example

In some of the above examples, the constraint equation is applied to data (such as one-channel data) in the same shape as the input signal (such as one-channel data).

Figure 16:
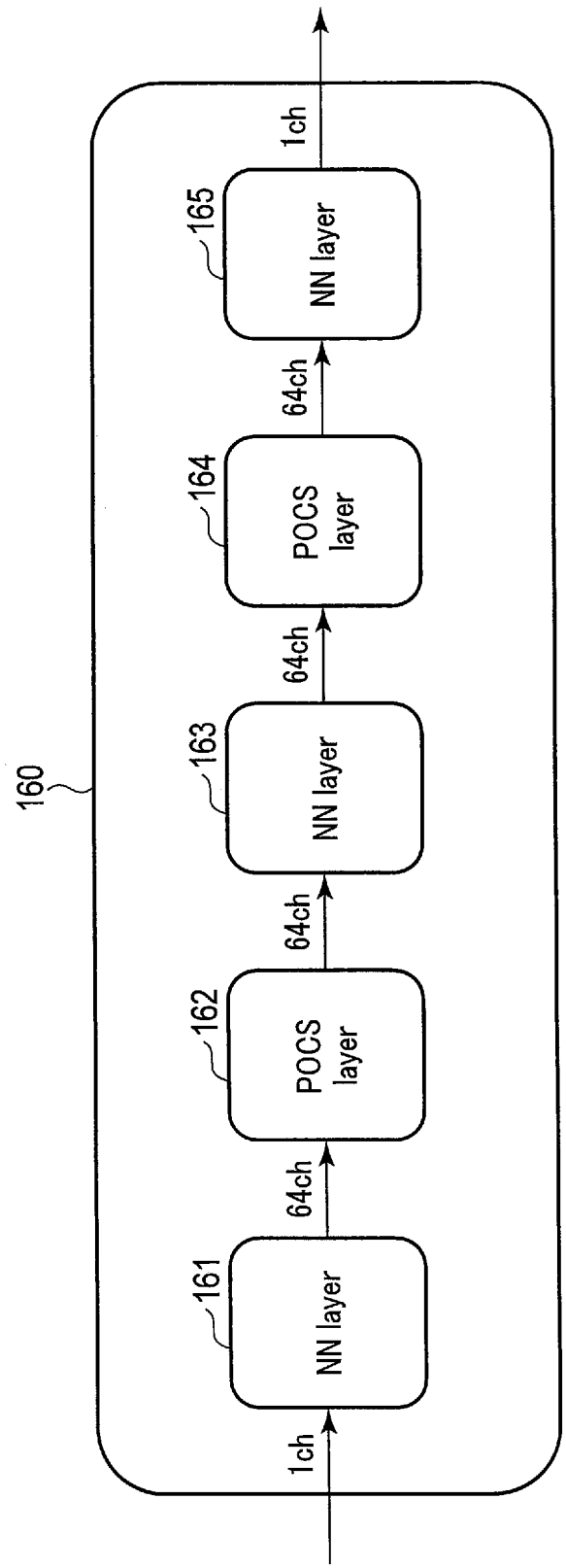
FIG. 16 shows a configuration example of a deep neural network according to a twelfth example.

FIG. 16 shows a configuration example of a deep neural network 160 according to the twelfth example. As shown in FIG. 16, the deep neural network 160 includes an NN layer 161, a POCS layer 162, an NN layer 163, a POCS layer 164, and an NN layer 165. The NN layer 161, the POCS layer 162, the NN layer 163, the POCS layer 164, and the NN layer 165 are connected in series. The POCS layer 162 and POCS layer 164 each apply a constraint equation on intermediate data (such as 64-channel data) in a different shape which is generated by the NN layer 161 and the NN layer 163.

Figure 17:
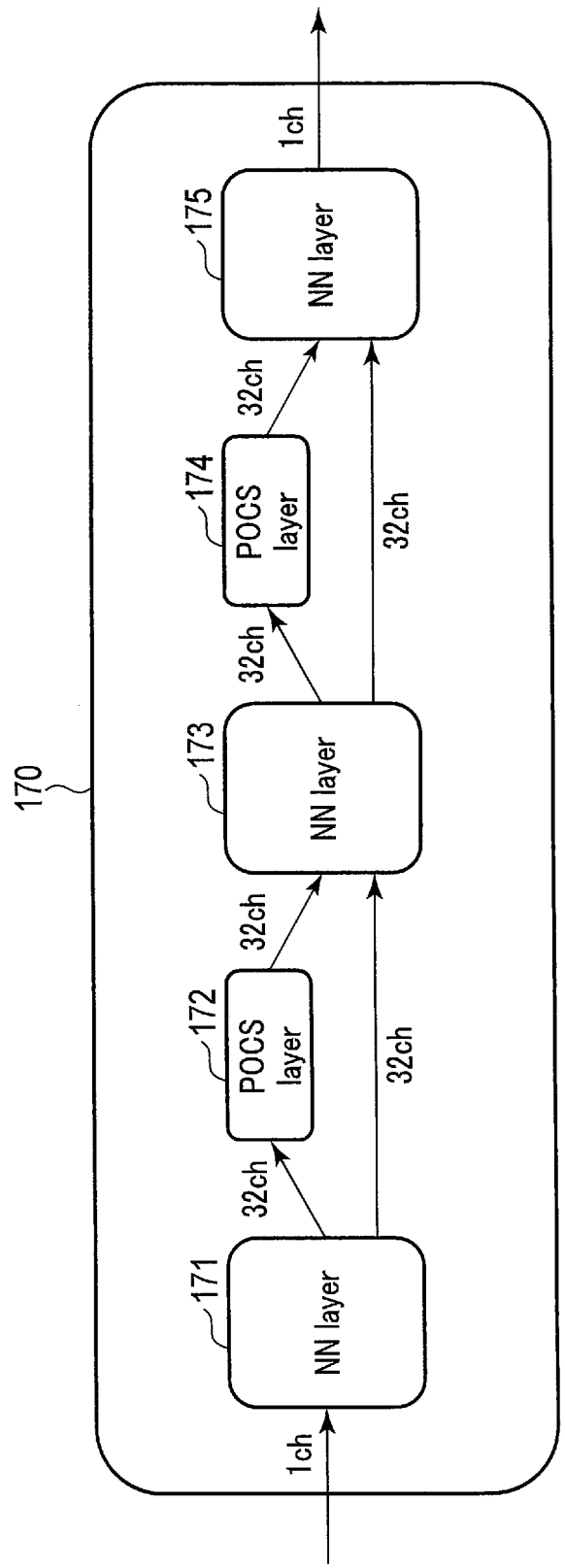
FIG. 17 shows a configuration example of another deep neural network according to the twelfth example.

FIG. 17 shows a configuration example of another deep neural network 170 according to the twelfth example. As shown in FIG. 17, the deep neural network 170 includes an NN layer 171, a POCS layer 172, an NN layer 173, a POCS layer 174, and an NN layer 175. The NN layer 171 and NN layer 173 have a path via the POCS layer 172 and a directly-connecting path. The NN layer 173 and NN layer 175 have a path via the POCS layer 174 and a directly-connecting path. The POCS layer 172 and POCS layer 174 each may apply a constraint equation on partial intermediate data (such as data of 32 channels of 64 channels) of intermediate data in a different shape which is generated by the NN layer 171 and the NN layer 173.

(Others)

The information processing apparatus 1 according to the present embodiment can also be implemented by combining the above-described first to twelfth examples as appropriate. For example, constraint terms based on at least two null bases of the null bases according to the first to twelfth examples may be incorporated into the error function.

According to at least one embodiment described above, a basis with a relatively low contribution rate can be utilized.

The term "processor" used in the above explanation means, for example, a CPU, a GPU, or circuitry such as an application specific integrated circuit (ASIC) or a programmable logic device (e.g., a simple programmable logic device (SPLD), a complex programmable logic device (CPLD), or a field programmable gate array (FPGA)). The processor reads and executes a program stored in memory circuitry to implement a function. Instead of storing a program in memory circuitry, a program may be directly incorporated in circuitry of the processor. In this case, the processor implements the function by reading and executing the program incorporated in the circuitry. The function corresponding to the program may be implemented by a combination of logic circuits instead of executing the program. Each processor of the present embodiment is not limited to the one configured as a single circuit; a plurality of independent circuits may be combined into one processor to implement the function of the processor. In addition, a plurality of structural elements in FIG. 1 may be integrated in one processor to implement the function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An information processing apparatus, comprising:
processing circuitry configured to:
generate a converted image by performing an image conversion on raw data obtained by imaging a subject with a medical scanning apparatus or an inspection apparatus,
calculate a plurality of bases by performing a basis conversion on the converted image as signal data;
select one or more specific bases with contribution rates lower than a reference from among the calculated plurality of bases;
generate, from the raw data, an output image that satisfies a constraint condition relating to projection amounts to the one or more specific bases; and
output the generated output image.

2. The information processing apparatus according to claim 1, wherein the processing circuitry is further configured to generate the output image from the raw data by performing, multiple times, an update operation to make an error function relatively small, the error function including a data consistency term based on a difference between the raw data and computational raw data that is based on an updated image and a projection amount of the updated image to each of the one or more specific bases.

3. The information processing apparatus according to claim 2, wherein the processing circuitry is further configured to minimize the error function under a constraint condition, wherein the projection amount is zero or smaller than or equal to a threshold.

4. The information processing apparatus according to claim 1, wherein the processing circuitry is further configured to:
generate a reduced-noise image by performing noise reduction processing on the output image,
generate computational raw data by performing a data conversion on the reduced-noise image, and
generate another output image by performing an image conversion on the computational raw data based on the reduced-noise image while using a specific space spanned by the one or more specific bases as a constraint condition.

5. The information processing apparatus according to claim 1, wherein
the signal data is image data, and
the processing circuitry is further configured to perform the basis conversion on the image data with respect to a temporal axis direction.

6. The information processing apparatus according to claim 5, wherein
the image data is a plurality of reconstructed images based on a plurality of k-space data items relating to a plurality of times, and
the processing circuitry is further configured to
calculate the plurality of bases by performing the basis conversion on the reconstructed images,
select the one or more specific bases from among the plurality of bases, and
generate a plurality of output images relating to the times by performing an image conversion on the k-space data items while using a specific space spanned by the one or more specific bases as a constraint condition.

7. The information processing apparatus according to claim 6, wherein each of the reconstructed images is a reconstructed image based on k-space data corresponding to a k-space line in a center part with respect to a phase encoding direction.

8. The information processing apparatus according to claim 1, wherein
the signal data is image data, and
the processing circuitry is further configured to perform the basis conversion on the image data with respect to an image space axis direction.

9. The information processing apparatus according to claim 8, wherein
the image data is a plurality of local images corresponding to a plurality of local areas set at different positions of a reconstructed image based on one k-space data item, and
the processing circuitry is further configured to:
calculate the plurality of bases by performing the basis conversion on the local images,
select the one or more specific bases from among the plurality of bases, and
generate an output image by performing an image conversion on the one k-space data item while using a specific space spanned by the one or more specific bases as a constraint condition.

10. The information processing apparatus according to claim 9, wherein the processing circuitry is further configured to repeat the calculating the plurality of bases, the selecting the one or more specific bases, and the generating the output image until a predetermined condition is met.

11. The information processing apparatus according to claim 1, wherein
the signal data is image data, and
the processing circuitry is further configured to perform the basis conversion on the image data with respect to a temporal axis direction and an image space axis direction.

12. The information processing apparatus according to claim 11, wherein
the image data includes first image data and second image data,
the first image data is a plurality of first reconstructed images based on a plurality of center lines extracted from a plurality of sparse k-space data items relating to a plurality of times, and
the second image data is a second reconstructed image based on k-space data generated by performing view sharing on the sparse k-space data items, and
the processing circuitry is further configured to:
calculate a plurality of first bases by performing the basis conversion on the first reconstructed images, and calculate a plurality of second bases by performing the basis conversion on the second reconstructed image,
select one or more specific first bases from among the first bases, and select one or more specific second bases from among the second bases, and
generate a plurality of output images relating to the times by performing an image conversion on the sparse k-space data items while using a specific first space spanned by the specific first bases and a specific second space spanned by the specific second bases as constraint conditions.

13. The information processing apparatus according to claim 1, wherein
the signal data is image data, and
the processing circuitry is further configured to perform the basis conversion on the image data with respect to a scan parameter value axis direction.

14. The information processing apparatus according to claim 1, wherein
the signal data is image data, and
the processing circuitry is further configured to perform the basis conversion on the image data with respect to a contrast axis direction.

15. The information processing apparatus according to claim 1, wherein the processing circuitry is further configured to generate the output image from the raw data under a constraint condition, wherein a projection amount of an updated image to a specific space spanned by the one or more specific bases is zero or noise.

16. The information processing apparatus according to claim 1, wherein the basis conversion performed by the processing circuitry is a principal component analysis, a singular value decomposition, an independent component analysis, a Fourier transform, or a discrete cosine transform.

17. The information processing apparatus according to claim 1, wherein the processing circuitry is further configured to;
generate image data as the signal data by performing the image conversion on first raw data, and
generate the output image by performing the image conversion on second raw data different from the first raw data while using a specific space spanned by the one or more specific bases as a constraint condition.

18. The information processing apparatus according to claim 1, wherein
the signal data is raw data, and
the processing circuitry is further configured to calculate the plurality of bases by performing the basis conversion on the raw data.

19. The information processing apparatus according to claim 1, wherein the processing circuitry is further configured to convert the signal data into a classification value utilizing the one or more specific bases.

20. The information processing apparatus according to claim 1, wherein the processing circuitry is further configured to perform a feature amount conversion utilizing projection onto convex sets on the one or more specific bases.

21. An information processing apparatus comprising:
processing circuitry configured to
generate MRS spectrum data based on raw data obtained by performing MRS imaging on a subject with an MRI apparatus;
calculate a plurality of bases by performing a basis conversion on the MRS spectrum data with respect to a frequency axis direction;

select one or more specific bases with contribution rates lower than a reference from among the calculated plurality of bases;
generate output spectrum data that satisfies a constraint condition relating to projection amounts to the one or more specific bases; and
output the generated output spectrum data.

22. The information processing apparatus according to claim 21, wherein
the MRS spectrum data includes a plurality of MRS spectra relating to a plurality of positions, and
the processing circuitry is further configured to:
calculate the plurality of bases by performing the basis conversion on the MRS spectra,
select the one or more specific bases from among the plurality of bases, and
generate a plurality of noise-reduced MRS spectra by performing, on the MRS spectra, noise reduction processing using a specific space spanned by the one or more specific bases as a constraint condition.

23. An information processing method, comprising:
generating a converted image by performing an image conversion on raw data obtained by imaging a subject with a medical scanning apparatus or an inspection apparatus;
calculating a plurality of bases by performing a basis conversion on the converted image as signal data;
selecting one or more specific bases with contribution rates lower than a reference from among the calculated plurality of bases;
generating, from the raw data, an output image that satisfies a constraint condition relating to projection amounts to the one or more specific bases; and
outputting the generated output image.

24. An information processing method, comprising:
processing circuitry configured to
generate a converted image by performing an image conversion on raw data obtained by imaging a subject with a medical scanning apparatus or an inspection apparatus;
calculate a plurality of bases by performing a basis conversion on the converted image as signal data;
select one or more specific bases with contribution rates lower than a reference from among the calculated plurality of bases;
calculate a feature amount sequence by performing an image conversion on the raw data using, as a constraint condition, a space spanned by the one or more specific bases;
convert the calculated feature amount sequence into a recognition result representing a classification value of each of a plurality of separately specified classes; and
output the recognition result.

* * * * *